(12) United States Patent
Aisaka et al.

(10) Patent No.: US 9,224,209 B2
(45) Date of Patent: Dec. 29, 2015

(54) IMAGE PROCESSING DEVICE AND METHOD, RECORDING MEDIUM AND PROGRAM

(75) Inventors: Kazuki Aisaka, Kanagawa (JP); Tomoyuki Ootsuki, Kanagawa (JP); Seiji Kobayashi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 501 days.

(21) Appl. No.: 13/594,382

(22) Filed: Aug. 24, 2012

(65) Prior Publication Data

US 2013/0108129 A1 May 2, 2013

(30) Foreign Application Priority Data

Aug. 31, 2011 (JP) ................. 2011-188277

(51) Int. Cl.
| | |
|---|---|
| *G06T 7/20* | (2006.01) |
| *G06T 15/00* | (2011.01) |
| *G06K 9/00* | (2006.01) |
| *G06K 9/48* | (2006.01) |

(52) U.S. Cl.
CPC .............. *G06T 7/20* (2013.01); *G06K 9/00208* (2013.01); *G06K 9/48* (2013.01); *G06T 7/2013* (2013.01); *G06T 7/2073* (2013.01); *G06T 7/2086* (2013.01); *G06T 15/00* (2013.01); *G06T 2207/30041* (2013.01)

(58) Field of Classification Search
CPC ....... G06T 7/20; G06T 7/2073; G06T 7/2086; G06T 15/00; G06T 2207/20201; G06T 7/0024; G06T 7/0026; G06T 7/0032; G06K 9/00208; G06K 9/00214
See application file for complete search history.

(56) References Cited

U.S. PATENT DOCUMENTS

| | | | | |
|---|---|---|---|---|
| 5,717,463 A | * | 2/1998 | Brailean et al. | 375/240.12 |
| 5,719,951 A | * | 2/1998 | Shackleton et al. | 382/118 |
| 5,734,737 A | * | 3/1998 | Chang et al. | 382/107 |
| 6,154,578 A | * | 11/2000 | Park et al. | 382/293 |
| 7,024,050 B2 | * | 4/2006 | Kondo et al. | 382/254 |
| 7,421,101 B2 | * | 9/2008 | Georgescu et al. | 382/128 |
| 7,426,285 B2 | * | 9/2008 | Pace | 382/103 |
| 7,440,619 B2 | * | 10/2008 | Mishima et al. | 382/209 |
| 7,751,479 B2 | * | 7/2010 | Paniconi et al. | 375/240.12 |
| 7,924,972 B2 | * | 4/2011 | Koehler et al. | 378/8 |
| 8,194,097 B2 | * | 6/2012 | Xiao et al. | 345/619 |
| 8,469,890 B2 | * | 6/2013 | Langeland et al. | 600/438 |
| 2001/0020946 A1 | * | 9/2001 | Kawakami et al. | 345/582 |

FOREIGN PATENT DOCUMENTS

| | | |
|---|---|---|
| JP | 2010-269016 A | 12/2010 |
| JP | 2011-087672 A | 5/2011 |

* cited by examiner

*Primary Examiner* — Manav Seth
(74) *Attorney, Agent, or Firm* — Hazuki International, LLC

(57) ABSTRACT

There is provided an image processing device including a motion vector detection portion that performs comparison of a substantially spherical photographic subject such that, among a plurality of captured images including the photographic subject, an image as a processing target and another image as a comparison target are compared using each of the plurality of captured images as the processing target, and which detects a motion vector of a whole three-dimensional spherical model with respect to the processing target, a motion compensation portion that performs motion compensation on the processing target, based on the motion vector of each of the plurality of captured images that is detected by the motion vector detection portion, and a synthesis portion that synthesizes each of the captured images that are obtained as a result of the motion compensation performed by the motion compensation portion.

9 Claims, 18 Drawing Sheets

IMAGE PROCESSING DEVICE AND METHOD, RECORDING MEDIUM AND PROGRAM

BACKGROUND

The present technology relates to an image processing device and method, a recording medium and a program, and particularly relates to an image processing device and method, a recording medium and a program that are capable of easily improving image quality of an image obtained by capturing a substantially spherical body, using a simple configuration.

A fundus examination is known in which a fundus oculi, such as a retina in an eyeball, an optic papilla or the like, is observed through a pupil. The fundus examination is performed using a special device, such as a funduscope or a fundus camera, for example. The fundus examination is performed such that, for example, when an image of the fundus oculi in the eyeball of a test subject is captured by a fundus camera and a resultant captured image (hereinafter referred to as a fundus oculi image) is displayed on a monitor or the like, an observer observes the fundus oculi image. In order for the observer to perform accurate observation, the image quality of the fundus oculi image is improved.

As a known technique to improve the image quality of the fundus oculi image, there is a technique in which, for example, data of a plurality of fundus oculi images that are sequentially captured are synthesized while taking into account the fact that the eyeball is a substantial sphere. With this technique, the plurality of fundus oculi images that are captured over a certain period of time are synthesized. Therefore, if the fundus oculi moves in the certain period of time, the image quality improvement of the fundus oculi image is hindered. To address this, Japanese Patent Application Publication No. JP-A-2011-087672 discloses a technique that performs alignment of rotation directions of a plurality of three-dimensional images of a fundus oculi. The three-dimensional images are formed using tomographic images of the fundus oculi that are obtained by optical coherence tomography (OCT). Further, for example, Japanese Patent Application Publication No. JP-A-2010-269016 discloses a technique that uses an affine transformation to perform alignment including rotation of a plurality of fundus oculi images.

SUMMARY

However, with the technique described in Japanese Patent Application Publication No. JP-A-2011-087672, the tomographic images by OCT are required in order to form the three-dimensional images, resulting in an increase in the device size. Further, with the technique described in Japanese Patent Application Publication No. JP-A-2010-269016, the affine transformation, which is used for rotation of two-dimensional images, is used for the fundus oculi images. As a result, it is difficult to accurately perform alignment of the images of the eyeball that is a three-dimensional sphere.

In summary, in recent years, there is a demand to easily obtain a fundus oculi image with a high image quality using a simple configuration. However, this demand is not sufficiently satisfied by known technologies including those described in Japanese Patent Application Publication No. JP-A-2011-087672 and Japanese Patent Application Publication No. JP-A-2010-269016. The above circumstances apply not only to the fundus oculi image, but also apply to an image obtained by capturing a substantially spherical body.

The present technology has been devised in light of the above circumstances, and makes it possible to easily improve image quality of an image obtained by capturing a substantially spherical body, using a simple configuration.

According to an embodiment of the present technology, there is provided an image processing device including a motion vector detection portion that performs comparison of a substantially spherical photographic subject such that, among a plurality of captured images including the photographic subject, an image as a processing target and another image as a comparison target are compared using each of the plurality of captured images as the processing target, and which detects a motion vector of a whole three-dimensional spherical model with respect to the processing target, a motion compensation portion that performs motion compensation on the processing target, based on the motion vector of each of the plurality of captured images that is detected by the motion vector detection portion, and a synthesis portion that synthesizes each of the captured images that are obtained as a result of the motion compensation performed by the motion compensation portion.

With respect to each of a plurality of blocks that are divided up from the processing target, the motion vector detection portion may detect a local motion vector by performing block matching with the comparison target. The motion vector detection portion may detect the motion vector of the whole three-dimensional spherical model with respect to the processing target, using the local motion vector of each of the plurality of blocks.

The motion vector detection portion may convert the local motion vector with respect to each of the plurality of blocks in the processing target into a local spherical motion vector in the three-dimensional spherical model. The motion vector detection portion may detect the motion vector of the whole three-dimensional spherical model with respect to the processing target, using the local spherical motion vector of each of the plurality of blocks.

The motion vector detection portion may convert each of the plurality of blocks in the processing target into a plurality of spherical blocks in the three-dimensional spherical model. With respect to each of the plurality of spherical blocks, the motion vector detection portion may detect, as the local motion vector, a local spherical motion vector by performing block matching with the comparison target. The motion vector detection portion may detect the motion vector of the whole three-dimensional spherical model with respect to the processing target, using the local spherical motion vector of each of the plurality of spherical blocks.

The motion vector detection portion may convert each of the processing target and the comparison target into a spherical image in the three-dimensional spherical model. The motion vector detection portion may perform matching between the spherical image of the processing target and the spherical image of the comparison target, and thereby may detect the motion vector of the whole three-dimensional spherical model with respect to the processing target.

The photographic subject may be a fundus oculi.

The three-dimensional spherical model may be switched and used in accordance with conditions of the photographic subject.

An image processing method, a recording medium and a program according to the embodiment of the present technology are the image processing method, the recording medium and the program corresponding to the image processing device according to the embodiment of the present technology described above.

In the image processing device and method, the recording medium and the program according to the embodiment of the present technology, comparison of a substantially spherical photographic subject is performed such that, among a plurality of captured images including the photographic subject, an image as a processing target and another image as a comparison target are compared using each of the plurality of captured images as the processing target, a motion vector of a whole three-dimensional spherical model with respect to the processing target is detected, motion compensation on the processing target is performed, based on the motion vector of each of the plurality of captured images that is detected, and each of the captured images that are obtained as a result of the motion compensation is synthesized.

According to another embodiment of the present technology, there is provided an image processing device including a conversion portion that, among a plurality of captured images that include a substantially spherical photographic subject, converts an image as a processing target and another image as a comparison target into spherical images on a three-dimensional spherical model, using each of the plurality of captured images as the processing target, an extraction portion that extracts features of each of the spherical image of the processing target and the spherical image of the comparison target, an alignment portion that aligns positions of the features such that the features match each other, and a synthesis portion that synthesizes each of the captured images that are obtained as a result of the alignment performed by the alignment portion.

A blood vessel shape may be used as the feature.

The photographic subject may be a fundus oculi.

The three-dimensional spherical model may be switched and used in accordance with conditions of the photographic subject.

An image processing method, a recording medium and a program according to another embodiment of the present technology are the image processing method, the recording medium and the program corresponding to the image processing device according to the embodiment of the present technology described above.

In the image processing device and method, the recording medium and the program according to the another embodiment of the present technology, among a plurality of captured images that include a substantially spherical photographic subject, an image as a processing target and another image as a comparison target are converted into spherical images on a three-dimensional spherical model, using each of the plurality of captured images as the processing target, features of each of the spherical image of the processing target and the spherical image of the comparison target are extracted, positions of the features are aligned such that the features match each other, and each of the captured images that are obtained as a result of the alignment are synthesized.

According to the present technology described above, it is possible to easily improve image quality of an image obtained by capturing a substantially spherical body, using a simple configuration.

DETAILED DESCRIPTION OF THE EMBODIMENT(S)

Hereinafter, four embodiments (hereinafter, respectively referred to as first to fourth embodiments) of the present technology will be explained in the following order.

1. First embodiment (an example in which a motion vector detected from each block is applied to a spherical model)

2. Second embodiment (an example in which a motion vector of each block applied to the spherical model is detected)

3. Third embodiment (an example in which a motion vector is detected from a fundus oculi image applied to the spherical model)

4. Fourth embodiment (an example in which fundus oculi images applied to the spherical model are aligned)

First Embodiment

Configuration Example of Fundus Oculi Image Processing Device

Figure 1:
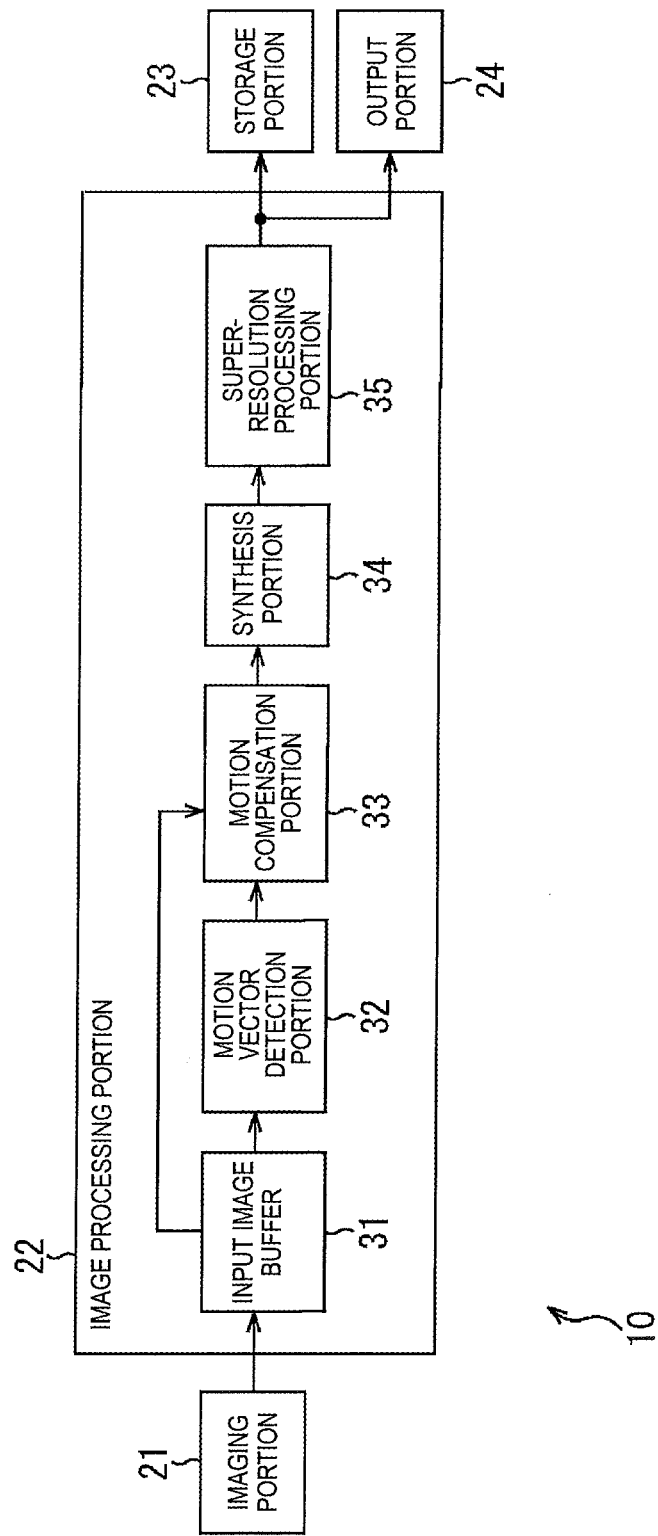
FIG. 1 is a block diagram showing a configuration example of a fundus oculi image processing device to which the present technology is applied.

FIG. 1 is a block diagram showing a configuration example of a fundus oculi image processing device to which the present technology is applied.

A fundus oculi image processing device 10 shown in FIG. 1 captures an image of a fundus oculi, such as a retina in an eyeball, an optic papilla or the like, of a test subject. The fundus oculi image processing device 10 performs image processing on data of the obtained fundus oculi image to improve image quality, and causes the fundus oculi image after the image processing to be displayed.

In order to reduce a burden on the test subject, the fundus oculi image processing device 10 captures an image of a photographic subject (namely, the fundus oculi of the test subject) while suppressing an amount of light irradiated onto the photographic subject. As a result, data of one sheet of a fundus oculi image can be obtained. However, in order to obtain a higher quality fundus oculi image, the fundus oculi image processing device 10 performs image capture of the photographic subject a plurality of times, and performs various types of image processing, which will be described later, on data of a plurality of captured images obtained each time. As a result of performing such various types of image processing, a fundus oculi image with higher image quality is displayed by the fundus oculi image processing device 10.

Note that the single image capture described herein means a series of operations of the fundus oculi image processing device 10 until light is accumulated on each of pixels of an imaging element and an electrical signal (data of each pixel) is output from each of the pixels. In this case, a number of times of image capture and a time interval between each image capture are not particularly limited. For example, if the time interval between each image capture is reduced to be approximately 1/30 seconds and image capture is performed 300 times consecutively at that time interval, 10 seconds of moving images are obtained. In summary, a plurality of times of image capture described herein is a concept including image capture to obtain a plurality of still images and image capture to obtain moving images.

The fundus oculi image processing device 10 configured in this manner includes an imaging portion 21, an image processing portion 22, a storage portion 23 and an output portion 24.

The imaging portion 21 captures an image of the fundus oculi of the test subject located at a predetermined position, as a photographic subject, and outputs data of the obtained fundus oculi image. For example, the imaging portion 21 can have a configuration including a charge coupled device (CCD) imaging element, a complementary metal oxide semiconductor (CMOS) imaging element and the like. However, the imaging portion 21 is not limited to this configuration, and it can have any configuration as long as it can output data of the fundus oculi image. Note that, in the present embodiment, the imaging portion 21 has a function of irradiating light onto the photographic subject that is being captured, in order to obtain a fundus oculi image with higher image quality.

As a technique to obtain a fundus oculi image with higher image quality, a technique is known in which the amount of light irradiated onto the fundus oculi of the test subject is increased during image capture. However, if the amount of light irradiated onto the fundus oculi of the test subject is increased during image capture, a burden on the test subject is increased. As a result, there is a possibility that an unnecessary influence will be exerted on an observation target or a psychological burden on the test subject will be increased. Further, in this case, since an increased amount of light is irradiated onto the fundus oculi of the test subject during image capture, the test subject feels that it is too bright and closes his/her eye or moves and there is a possibility that the fundus oculi image with high image quality cannot be obtained. To address this, in the present embodiment, the amount of light irradiated onto the fundus oculi is not increased during image capture, and the imaging portion 21 repeats image capture of the fundus oculi a plurality of times while maintaining a state in which low-intensity light is irradiated onto the fundus oculi. Note that image capture of the fundus oculi by the imaging portion 21 may be performed a plurality of times to obtain still images or may be performed once to obtain moving images.

Each of the fundus oculi images obtained by the single image capture in this manner has low image quality because the light irradiated during image capture is weak (dark). For this reason, in the present embodiment, the image processing portion 22 performs predetermined image processing on data of the fundus oculi images obtained by each of the plurality of times of image capture by the imaging portion 21, and thus generates and outputs data of one sheet of a fundus oculi image with high image quality. Note that, in this case, the improvement in image quality becomes easier when the plurality of fundus oculi images, which are image processing targets, are more similar to each other. Therefore, it is preferable to reduce a time taken to perform a plurality of times of imaging operations of the imaging portion 21.

The image processing portion 22 causes the data of the fundus oculi image after the image processing, namely, the data of the fundus oculi image with high image quality, to be stored in the storage portion 23 or to be output from the output portion 24.

The storage portion 23 is formed by, for example, a hard disk, a flash memory or a random access memory (RAM), and stores the data of the fundus oculi image supplied from the image processing portion 22. The data of the fundus oculi image stored in the storage portion 23 is read by a playback portion or the like (not shown in the drawings), and is output to the output portion 24 for display or transmitted to another device. Other image processing is performed on the data of the fundus oculi image by an image processing portion (not shown in the drawings) other than the image processing portion 22.

The output portion 24 includes a monitor, such as a cathode ray tube (CRT), a liquid crystal display (LCD) or the like, and an output terminal etc. The output portion 24 outputs and displays on the monitor the data of the fundus oculi image output from the image processing portion 22, or outputs the data to an external device from the output terminal of the output portion 24.

Further, hereinafter, a detailed configuration of the image processing portion 22 included in the fundus oculi image processing device 10 shown in FIG. 1 will be explained. The image processing portion 22 includes an input image buffer 31, a motion vector detection portion 32, a motion compensation portion 33, a synthesis portion 34 and a super-resolution processing portion 35.

The input image buffer 31 is configured as one region of a given storage medium, such as a hard disk, a flash memory or a RAM, for example. The input image buffer 31 holds data of fundus oculi images with low image quality that are sequentially supplied from the imaging portion 21, as respective data of input images. The data of each of the input images is read out from the input image buffer 31 at a predetermined timing and is supplied to the motion vector detection portion 32 or the motion compensation portion 33.

The data of the fundus oculi images obtained by the imaging portion 21 are obtained by performing image capture a plurality of times, and the fundus oculi images are not necessarily exactly the same as each other. For example, it is conceivable that a positional displacement occurs in some or all of the fundus oculi images. Accordingly, if the plurality of fundus oculi images are simply synthesized, there is a possibility that the resultant fundus oculi image becomes a blurred image or a double image due to the positional displacement or the like. Therefore, before the synthesis portion 34 synthesizes the data of the plurality of fundus oculi images, it is necessary that the motion vector detection portion 32 detects a motion vector and the motion compensation portion 33 performs motion compensation using the motion vector to thereby reduce a difference (a positional displacement etc.) between the images to be synthesized.

The motion vector detection portion 32 reads out data of a processing target input image and data of an input image that is captured at a different time from the processing target input image, from the input image buffer 31. Next, the motion vector detection portion 32 compares the read-out data of the two sheets of input images and thereby detects a motion vector of the whole fundus oculi in the processing target input image. Note that, as a motion vector detection technique, the present embodiment adopts a technique in which the eyeball is modeled as a three-dimensional sphere and a motion vector of the whole sphere is detected. More specifically, among the plurality of captured images including the substantially spherical photographic subject, the motion vector detection portion 32 performs comparison of the captured image as a processing target and the captured image as a comparison target, using a three-dimensional spherical model (hereinafter simply referred to as a spherical model) of the photographic subject. The comparison is performed using each of the plurality of captured images as a processing target. This technique will be described later with reference to FIG. 2, along with a detailed configuration of the motion vector detection portion 32.

The motion compensation portion 33 reads out the data of the processing target input image from the input image buffer 31. At the same time, the motion compensation portion 33 acquires, from the motion vector detection portion 32, the motion vector of the whole fundus oculi in the processing target input image. Then, the motion compensation portion 33 uses the motion vector of the whole fundus oculi to perform motion compensation on the data of the processing target input image. The motion compensation is processing that moves the processing target input image on the spherical model in accordance with the motion vector of the whole fundus oculi in the processing target input image. By doing this, a difference (a positional displacement etc.) between the plurality of fundus oculi images is reduced. Data of fundus oculi images after the motion compensation is supplied to the synthesis portion 34.

In this manner, the respective data of the plurality of fundus oculi images obtained by the imaging portion 21 performing image capture a plurality of times are sequentially used as a processing target, and after the motion compensation portion 33 performs motion compensation on the respective data, they are sequentially supplied to the synthesis portion 34.

When all the data of the plurality of fundus oculi images are supplied from the motion compensation portion 33, the synthesis portion 34 synthesizes the data of the plurality of fundus oculi images and thereby generates data of one sheet of a fundus oculi image. The synthesis portion 34 supplies the generated data to the super-resolution processing portion 35.

The super-resolution processing portion 35 performs super-resolution processing on the data of the fundus oculi image synthesized by the synthesis portion 34, and thereby generates data of the fundus oculi image with a higher resolution than that at the time of synthesis. Note that any processing method can be used to perform the super-resolution processing by the super-resolution processing portion 35. For example, a method described in Japanese Patent Application Publication No. JP-A-2010-102696, or a method described in Japanese Patent Application Publication No. JP-A-2010-103981 may be used to perform the super-resolution processing. Note however that, in the super-resolution processing, processing in accordance with features of a living organism is performed so that a higher-resolution image with less noise can be obtained. The data of the high-resolution fundus oculi image generated in this manner by the super-resolution processing portion 35 is stored in the storage portion 23 or output from the output portion 24.

Next, a detailed configuration of the motion vector detection portion 32 will be explained.

Configuration Example and Processing of Motion Vector Detection Portion

Figure 2:
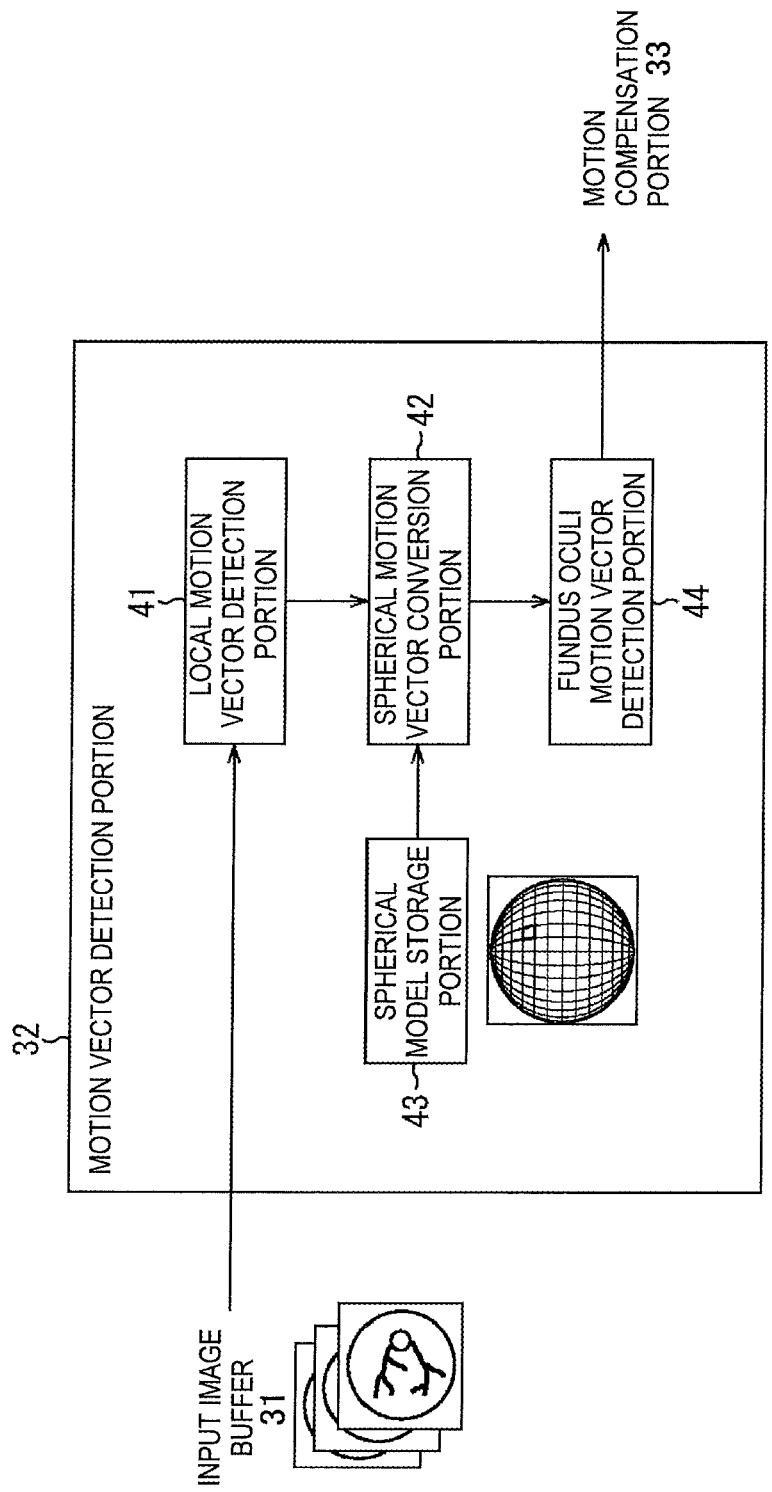
FIG. 2 is a block diagram showing a configuration example of a motion vector detection portion.
Figure 3:
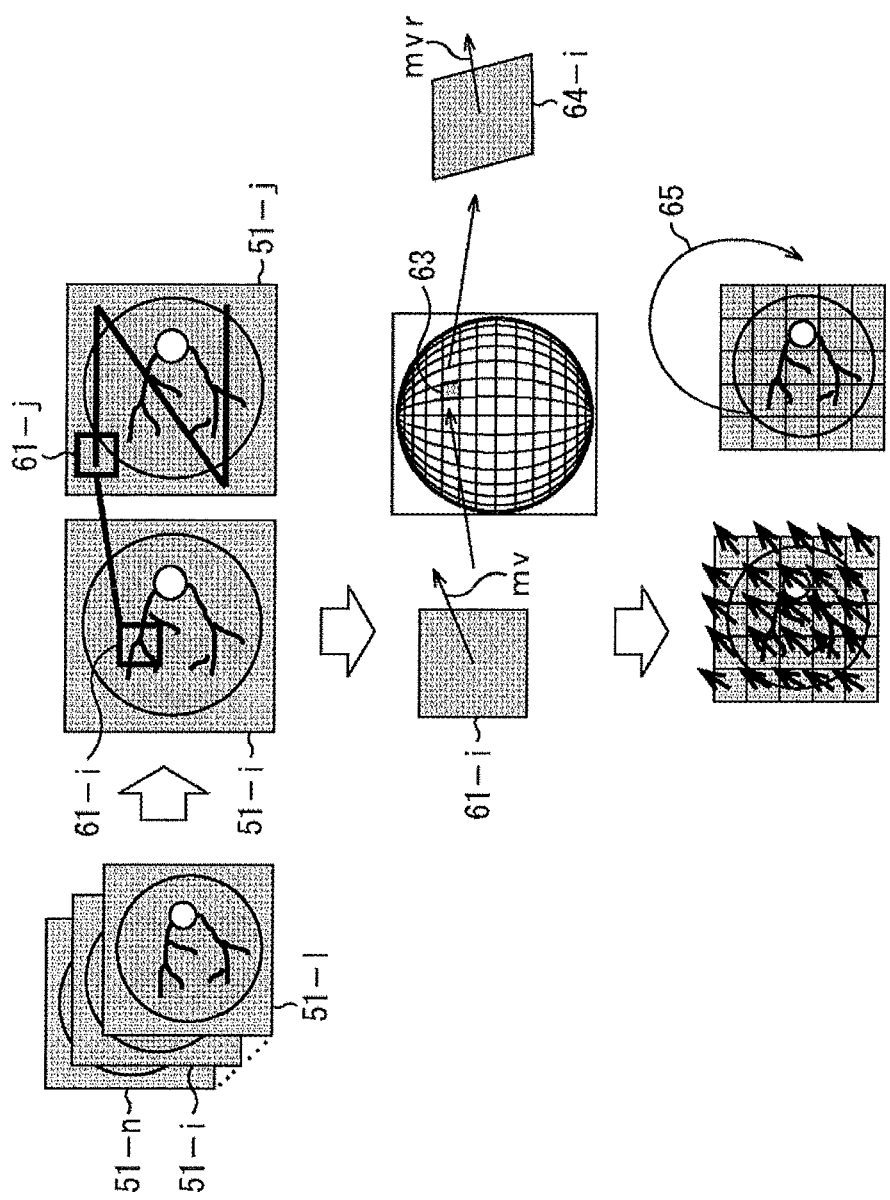
FIG. 3 is a diagram illustrating specific processing of the motion vector detection portion.

FIG. 2 is a block diagram showing a configuration example of the motion vector detection portion 32. FIG. 3 is a diagram illustrating specific processing of the motion vector detection portion 32.

As shown in FIG. 2, the motion vector detection portion 32 includes a local motion vector detection portion 41, a spherical motion vector conversion portion 42, a spherical model storage portion 43 and a fundus oculi motion vector detection portion 44.

The local motion vector detection portion 41 reads out data of a processing target fundus oculi image 51-$i$ and data of a comparison target fundus oculi image 51-$j$ that is different from the processing target, from among respective data of n sheets of fundus oculi images 51-$l$ to 51-$n$ that are respectively held as input image data in the input image buffer 31 as shown in FIG. 3. Here, n is an integer equal to or larger than 2 and indicates a total number of the input images held in the input image buffer 31. i is an integer equal to or larger than 1 and equal to or smaller than n−1. j is an integer equal to or larger than 1 and equal to or smaller than n, and is an integer different from the integer i. For example, in the present embodiment, j=i+1 is set. In summary, an image adjacent to a processing target image is used as a comparison target.

The local motion vector detection portion 41 divides up the processing target fundus oculi image 51-$i$ into a plurality of blocks having a prescribed size, and sequentially sets each of the plurality of blocks as a processing target block 61-$i$.

The local motion vector detection portion 41 also divides up the comparison target fundus oculi image 51-$j$ into a plurality of blocks having a prescribed size, in a similar manner to the above. Each time the local motion vector detection portion 41 sets each of the plurality of blocks as a comparison target block 61-$j$ in a raster scan order, for example, the local motion vector detection portion 41 repeatedly calculates a degree of similarity between the processing target block 61-$i$ and the comparison target block 61-$j$. In summary, so-called block matching is performed.

The local motion vector detection portion 41 detects local motion in the processing target block 61-$i$, as a motion vector mv, based on a positional relationship between the processing target block 61-$i$ and the comparison target block 61-$j$ matched with (namely, having a highest degree of similarity with) the processing target block 61-$i$.

The spherical motion vector conversion portion 42 applies the processing target block 61-$i$ to a spherical model 63 that is stored in the spherical model storage portion 43, as shown in FIG. 3. By doing this, the processing target block 61-$i$ is converted into a predetermined block 64-$i$ on the spherical model 63. Note that the converted block 64-$i$ is hereinafter referred to as a spherical processing target block 64-$i$. In this case, the motion vector mv in the processing target block 61-$i$ is converted into a motion vector mvr in the spherical processing target block 64-$i$. Note that the motion vector mvr after the conversion is hereinafter referred to as a spherical motion vector mvr.

This type of the spherical motion vector mvr is obtained by repeatedly performing the above-described series of processing for each of the plurality of blocks divided up from the processing target fundus oculi image 51-*i*.

With respect to the processing target fundus oculi image 51-*i*, the fundus oculi motion vector detection portion 44 detects a motion vector 65 of the whole fundus oculi, based on the spherical motion vector mvr of each of the plurality of blocks. The fundus oculi motion vector detection portion 44 supplies to the motion compensation portion 33 the motion vector 65 of the whole fundus oculi in the processing target fundus oculi image 51-*i*.

Thus, motion compensation using the motion vector 65 of the whole fundus oculi is performed on the data of the processing target fundus oculi image 51-*i* by the motion compensation portion 33, as described above with reference to FIG. 1.

The configuration of the fundus oculi image processing device 10 is explained above with reference to FIG. 1 to FIG. 3. Next, processing (hereinafter referred to as fundus oculi image generation processing) that is performed by the fundus oculi image processing device 10 configured as described above will be explained with reference to FIG. 4.

Flow of Fundus Oculi Image Generation Processing

Figure 4:
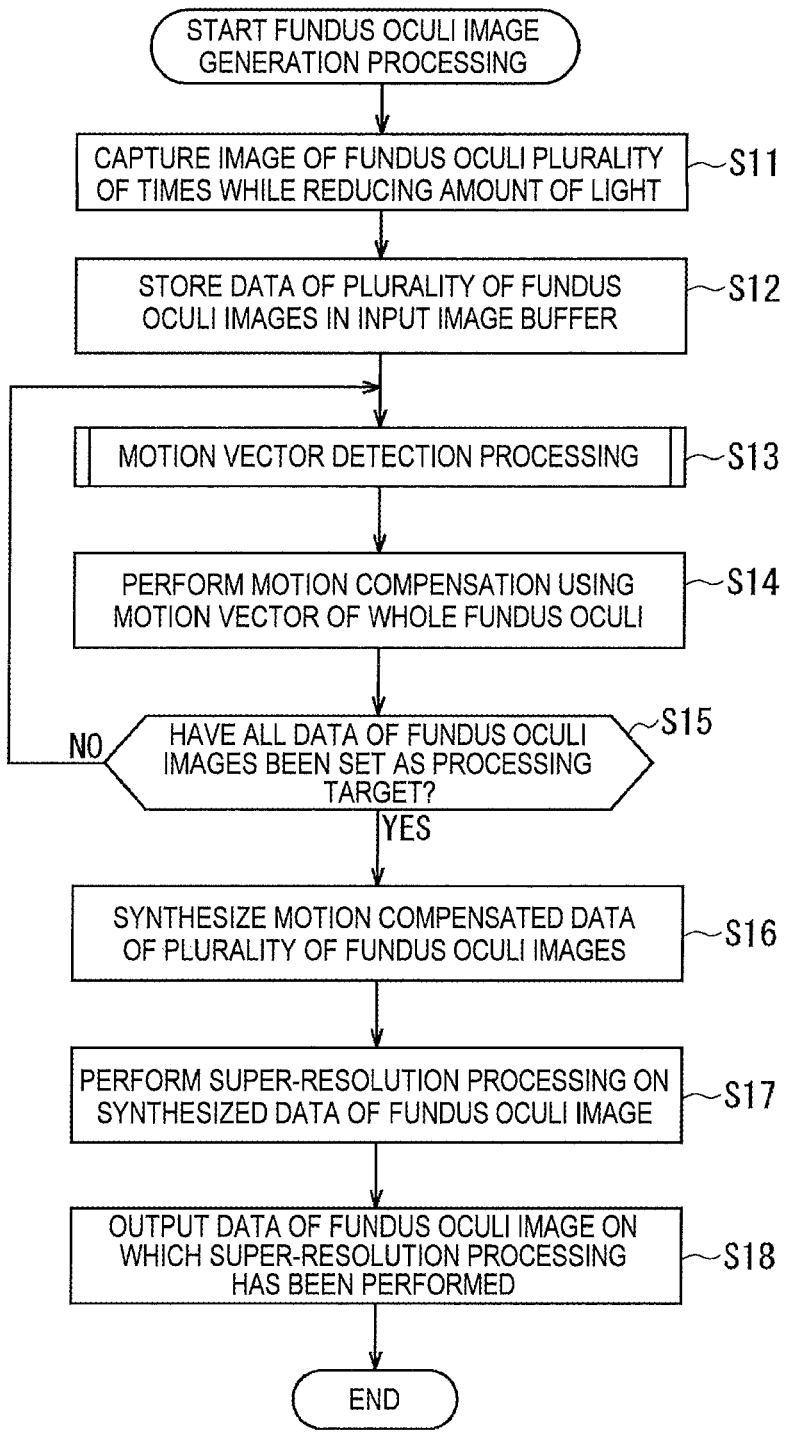
FIG. 4 is a flowchart illustrating a flow of fundus oculi image generation processing.

FIG. 4 is a flowchart illustrating a flow of the fundus oculi image generation processing.

At step S11, the imaging portion 21 reduces the amount of light and captures an image of the fundus oculi of the test subject a plurality of times. Note that, as described above, image capture of the fundus oculi by the imaging portion 21 may be performed a plurality of times to obtain still images or may be performed once to obtain moving images.

At step S12, the image processing portion 22 causes the input image buffer 31 to store the data of the plurality of fundus oculi images with low image quality obtained by the processing at step S11.

At step S13, the motion vector detection portion 32 performs motion vector detection processing and detects the motion vector of the whole fundus oculi. Note that the motion vector detection processing will be described in more detail later with reference to FIG. 5.

At step 14, the motion compensation portion 33 uses the motion vector of the whole fundus oculi detected by the processing at step S13 to perform motion compensation on the data of the processing target input image read out from the input image buffer 31. Note that the motion compensation portion 33 performs similar motion compensation also on the data of the input image on which the processing has been performed.

At step S15, the image processing portion 22 determines whether or not all the data of the fundus oculi images have been set as the processing target. In the present embodiment, the data of the processing target fundus oculi images are respective data of the fundus oculi images 51-*l* to 51-(*n*–1). Therefore, the data of the comparison target fundus oculi images are respective data of the fundus oculi images 51-2 to 51-*n*.

When all the data of the fundus oculi images have not yet been set as the processing target, NO is determined at step S15 and the processing is returned to step S13. Then, the processing from step S13 onward is repeated. More specifically, loop processing from step S13 to step S15 is repeated until all the data of the fundus oculi images are set as the processing target. For example, as described later with reference to FIG. 5, if a motion vector is detected for the fundus oculi image 51-2, which is the comparison target of the fundus oculi image 51-1 set as the processing target by the motion vector detection processing at step S13, then the fundus oculi image 51-2 is set as the processing target image, and a motion vector for an adjacent comparison target fundus oculi image 51-3 is detected. This type of processing is sequentially repeated.

After that, when all the data of the fundus oculi images have been set as the processing target, YES is determined at step S15 and the processing proceeds to step S16.

At step S16, the synthesis portion 34 synthesizes the motion compensated data of the plurality of the fundus oculi images. Thus, data of one sheet of a fundus oculi image is generated from the data of the n sheets of fundus oculi images.

At step S17, the super-resolution processing portion 35 performs super-resolution processing on the synthesized data of the fundus oculi image. Thus, data of the fundus oculi image with a higher resolution than that at the time of synthesis at step S16 is generated.

At step S18, the image processing portion 22 causes the storage portion 23 to store the data of the fundus oculi image on which the super-resolution processing has been performed, or causes the output portion 24 to output the data.

This completes the fundus oculi image generation processing. Next, the motion vector detection processing at step S13 will be explained.

Flow of Motion Vector Detection Processing

Figure 5:
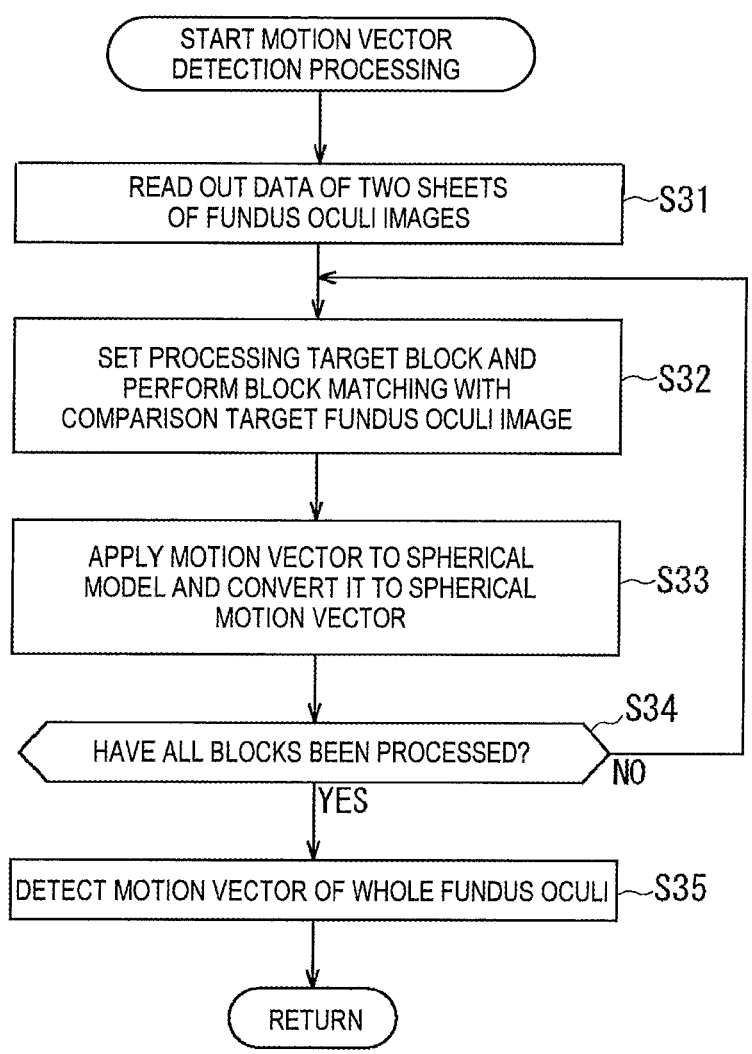
FIG. 5 is a flowchart illustrating a flow of motion vector detection processing.

FIG. 5 is a flowchart illustrating a flow of the motion vector detection processing performed at step S13 shown in FIG. 4.

At step S31, the local motion vector detection portion 41 reads out data of two sheets of fundus oculi images, which are a processing target and a comparison target, from the input image buffer 31. For example, data of two sheets of adjacent fundus oculi images, the fundus oculi image 51-1 and the fundus oculi image 51-2, are read out.

At step S32, the local motion vector detection portion 41 sets a processing target block from a processing target image (for example, the fundus oculi image 51-1) and performs block matching with a comparison target fundus oculi image (for example, the fundus oculi image 51-2). As a result, a motion vector in the processing target block is detected.

At step S33, the spherical motion vector conversion portion 42 applies the motion vector detected at step S32 to the spherical model stored in the spherical model storage portion 43, and thereby converts the motion vector to a spherical motion vector.

At step S34, the motion vector detection portion 32 determines whether or not all the blocks have been processed. More specifically, the motion vector detection portion 32 determines whether or not spherical motion vectors corresponding to all the blocks divided up from a sheet of the processing target fundus oculi image (for example, the sheet of the fundus oculi image 51-1 read out by the processing at step S31) have been detected.

When all the blocks have not yet been processed, NO is determined at step S34 and the processing is returned to step S32. Then, the processing from step S32 onward is repeated. More specifically, loop processing from step S32 to step S34 is repeated until all the blocks are processed.

After that, when all the blocks have been processed, YES is determined at step S34 and the processing proceeds to step S35.

At step S35, with respect to the processing target fundus oculi image (for example, the sheet of the fundus oculi image 51-1 read out by the processing at step S31), the fundus oculi motion vector detection portion 44 detects a motion vector of the whole fundus oculi based on the respective spherical motion vectors of the plurality of blocks.

This completes the motion vector detection processing.

In this manner, the image processing using a spherical model is performed on the plurality of fundus oculi images that are obtained while suppressing the amount of irradiated light in order to reduce a burden on the test subject. Thus, data of one sheet of a fundus oculi image with high image quality is generated.

In the present embodiment, general block matching is used as degree of similarity calculation between the processing target block divided up from the processing target fundus oculi image and the comparison target block divided up from the comparison target fundus oculi image. Since this type of general block matching is applied, high-speed processing can be easily achieved. Further, since the block matching is performed for each of the processing target blocks, it is possible to reduce a memory amount to be used.

Second Embodiment

In the motion vector detection portion 32 of the first embodiment, a spherical model is applied to the motion vector in the processing target block detected by block matching. However, the target to which the spherical model is applied is not limited to this example. For example, the spherical model may be applied to the processing target block before the block matching is performed and the block matching may be performed thereafter.

Note that a fundus oculi image processing device according to a second embodiment has basically the same function and configuration as those of the fundus oculi image processing device 10 shown in FIG. 1. Therefore, hereinafter, an explanation of same portions as those of the fundus oculi image processing device 10 shown in FIG. 1 is omitted, and a different portion only, namely, a motion vector detection portion 70 that differs from the motion vector detection portion 32 of the fundus oculi image processing device 10 shown in FIG. 1, will be explained.

Configuration Example and Processing of Motion Vector Detection Portion 70

Figure 6:
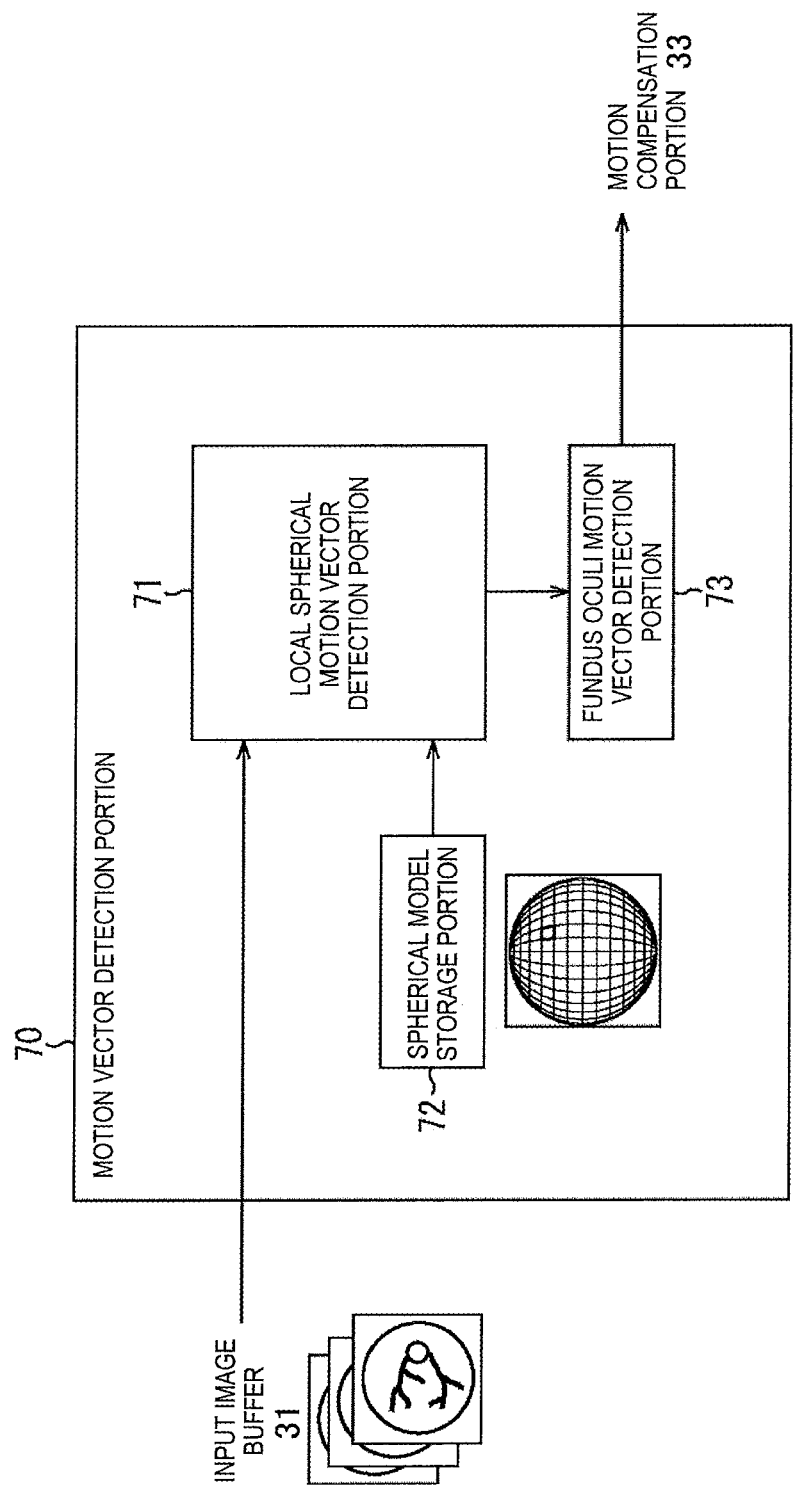
FIG. 6 is a block diagram showing a configuration example of a motion vector detection portion.
Figure 7:
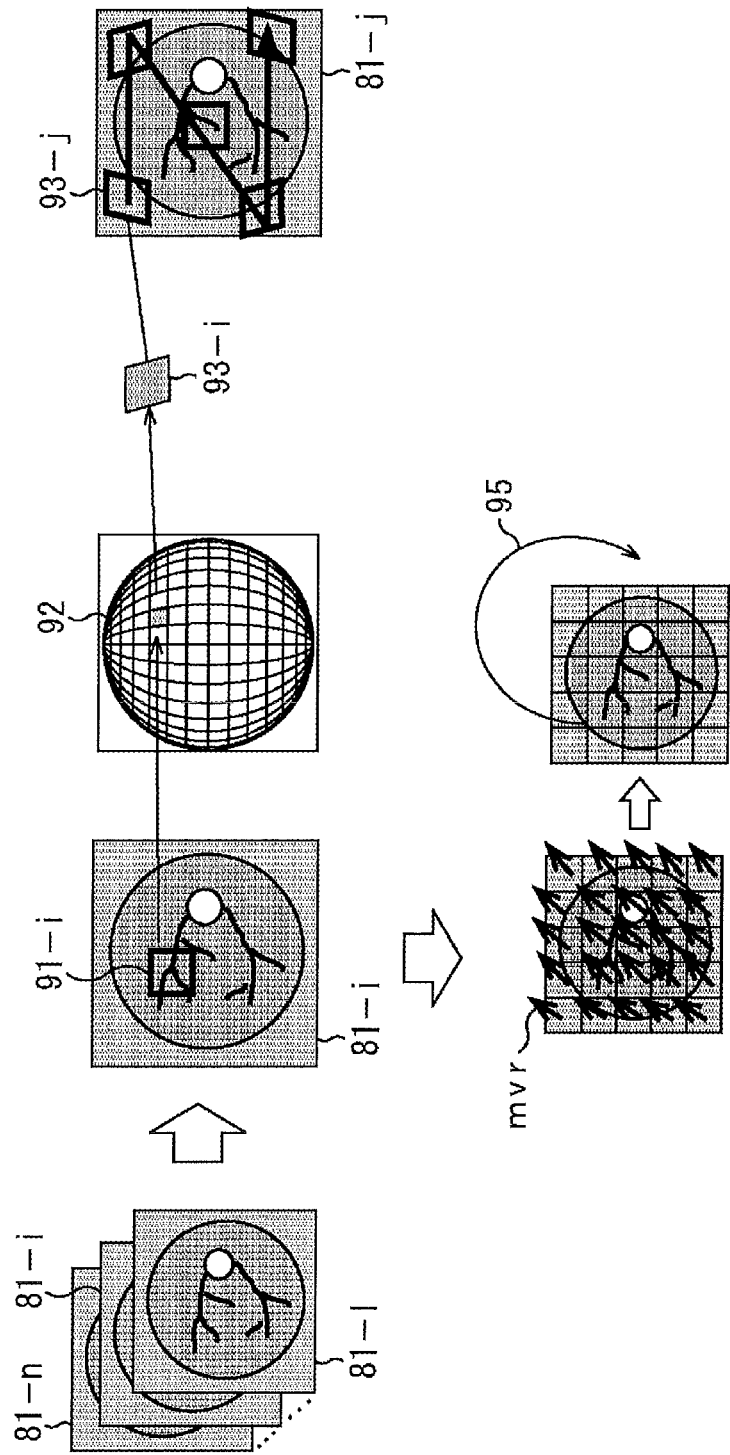
FIG. 7 is a diagram illustrating specific processing of the motion vector detection portion.

FIG. 6 is a block diagram showing a configuration example of the motion vector detection portion 70. FIG. 7 is a diagram illustrating specific processing of the motion vector detection portion 70.

As shown in FIG. 6, the motion vector detection portion 70 includes a local spherical motion vector detection portion 71, a spherical model storage portion 72 and a fundus oculi motion vector detection portion 73.

The local spherical motion vector detection portion 71 reads out data of a processing target fundus oculi image 81-$i$ and data of a comparison target fundus oculi image 81-$j$ that is different from the processing target, from among respective data of n sheets of fundus oculi images 81-$l$ to 81-$n$ that are respectively held as input image data in the input image buffer 31, as shown in FIG. 7. Here, n is an integer equal to or larger than 2 and indicates a total number of the input images held in the input image buffer 31. i is an integer equal to or larger than 1 and equal to or smaller than n. j is an integer equal to or larger than 1 and equal to or smaller than n, and is an integer different from the integer i.

The local spherical motion vector detection portion 71 divides up the processing target fundus oculi image 81-$i$ into a plurality of blocks having a prescribed size, and sequentially sets each of the plurality of blocks as a processing target block 91-$i$.

The local spherical motion vector detection portion 71 applies the processing target block 91-$i$ to a spherical model 92 that is stored in the spherical model storage portion 72, as shown in FIG. 7. By doing this, the processing target block 91-$i$ is converted into a predetermined block 93-$i$ on the spherical model 92. Note that the converted block 93-$i$ is hereinafter referred to as the processing target spherical block 93-$i$.

The local spherical motion vector detection portion 71 also divides up the comparison target fundus oculi image 81-$j$ into a plurality of blocks having a prescribed size, in a similar manner to the above. Each time the local spherical motion vector detection portion 71 sets each of the plurality of blocks as a comparison target block 91-$j$ in a raster order, for example, the local spherical motion vector detection portion 71 also applies the comparison target block 91-$j$ to the spherical model 92. By doing this, the comparison target block 91-$j$ is converted into a predetermined block 93-$j$ on the spherical model 92. Note that the converted block 93-$j$ is hereinafter referred to as the comparison target spherical block 93-$j$.

The local spherical motion vector detection portion 71 repeatedly calculates a degree of similarity between the processing target spherical block 93-$i$ and the comparison target spherical block 93-$j$. In summary, so-called block matching is performed.

The local spherical motion vector detection portion 71 detects local motion of the sphere in the processing target spherical block 93-$i$, as the spherical motion vector mvr, based on a positional relationship between the processing target spherical block 93-$i$ and the comparison target spherical block 93-$j$ matched (namely, having a highest degree of similarity) with the processing target spherical block 93-$i$.

This type of the spherical motion vector mvr is obtained by repeatedly performing the above-described series of processing for each of the plurality of blocks divided up from the processing target fundus oculi image 81-$i$.

With respect to the processing target fundus oculi image 81-$i$, the fundus oculi motion vector detection portion 73 detects a motion vector 95 of the whole fundus oculi, based on the respective spherical motion vectors mvr of the plurality of blocks. The fundus oculi motion vector detection portion 73 supplies the motion vector 95 of the whole fundus oculi in the processing target fundus oculi image 81-$i$ to the motion compensation portion 33.

Thus, motion compensation using the motion vector 95 of the whole fundus oculi is performed on the data of the processing target fundus oculi image 81-$i$ by the motion compensation portion 33, as described above with reference to FIG. 1.

Next, an explanation will be given of fundus oculi image generation processing of the fundus oculi image processing device 10 according to the second embodiment that has the motion vector detection portion 70 configured in this manner. The fundus oculi image generation processing according to the second embodiment is performed in accordance with the flowchart shown in FIG. 4, in a similar manner to the first embodiment. However, content of motion vector detection processing at step S13 in the second embodiment is different from that in the first embodiment. Therefore, hereinafter, the motion vector detection processing at step S13 in the second embodiment will be explained with reference to FIG. 8.

Flow of Motion Vector Detection Processing

Figure 8:
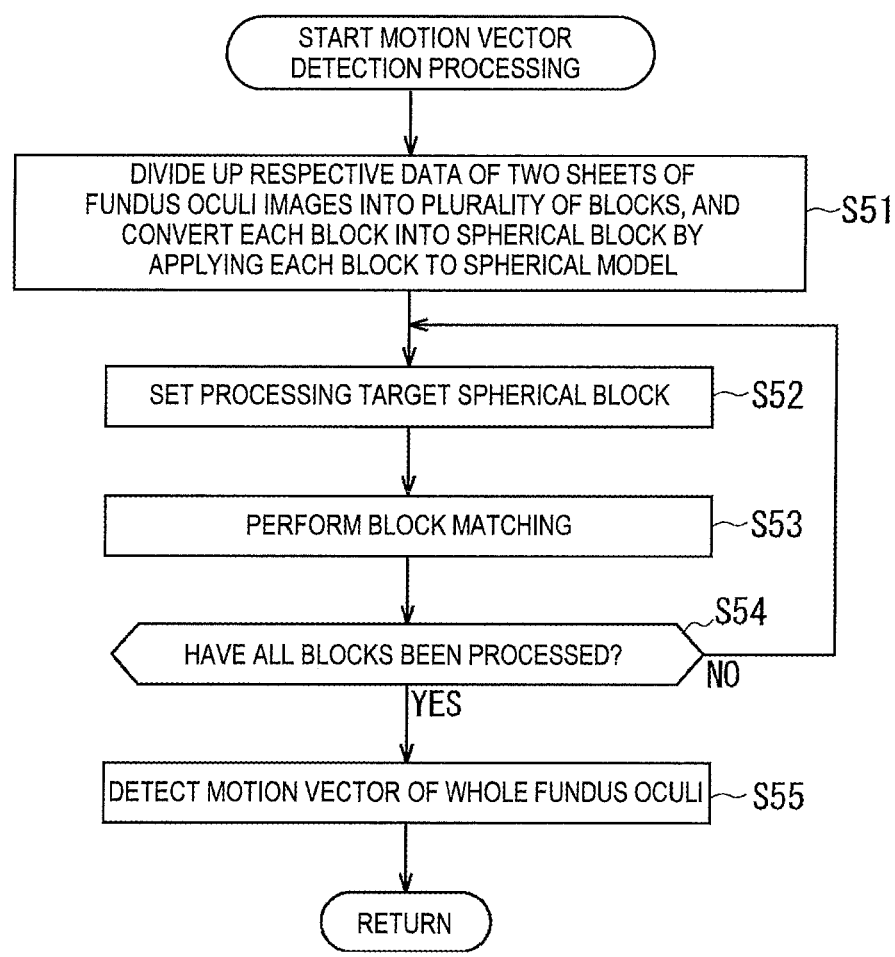
FIG. 8 is a flowchart illustrating a flow of motion vector detection processing.

FIG. 8 is a flowchart illustrating a flow of the motion vector detection processing.

At step S51, the local spherical motion vector detection portion 71 divides up the respective data of the two sheets of fundus oculi images (which are the processing target and the comparison target) read out from the input image buffer 31 into a plurality of blocks. The local spherical motion vector detection portion 71 applies each of the plurality of blocks to a spherical model and converts each of the plurality of blocks to a spherical block.

At step S52, the local spherical motion vector detection portion 71 sets a processing target spherical block from the processing target fundus oculi image.

At step S53, the local spherical motion vector detection portion 71 performs block matching between the processing target spherical block and a comparison target spherical block. Thus, a spherical motion vector in the processing target spherical block is detected.

At step S54, the motion vector detection portion 70 determines whether or not all the blocks have been processed. More specifically, the motion vector detection portion 70 determines whether or not spherical motion vectors corresponding to all the blocks divided up from one sheet of the processing target fundus oculi image have been detected.

When all the blocks have not yet been processed, NO is determined at step S54 and the processing is returned to step S52. Then, the processing from step S52 onward is repeated. More specifically, loop processing from step S52 to step S54 is repeated until all the blocks are processed.

After that, when all the blocks have been processed, YES is determined at step S54 and the processing proceeds to step S55.

At step S55, with respect to the processing target fundus oculi image, the fundus oculi motion vector detection portion 73 detects a motion vector of the whole fundus oculi based on the respective spherical motion vectors of the plurality of blocks.

This completes the motion vector detection processing.

In the present embodiment, block matching is performed after the processing target block divided up from the processing target fundus oculi image and the comparison target block divided up from the comparison target fundus oculi image have each been applied to the spherical model. Therefore, the blocks on the spherical model are used in the degree of similarity calculation between the processing target fundus oculi image and the comparison target fundus oculi image. Thus, the motion vector of the whole fundus oculi, which is a substantially spherical body, can be detected accurately. Since the image processing using this motion vector is performed on the captured fundus oculi images, a fundus oculi image with higher image quality is generated in comparison with the first embodiment.

Third Embodiment

In the motion vector detection portions 32 and 70 according to the first and second embodiments, the spherical model is applied to the processing target block divided up from the processing target image. However, the target to which the spherical model is applied is not limited to this example. For example, the spherical model may be applied to the whole fundus oculi image and thereafter matching may be performed.

Note that a fundus oculi image processing device according to a third embodiment has basically the same function and configuration as those of the fundus oculi image processing device 10 shown in FIG. 1. Therefore, hereinafter, an explanation of same portions as those of the fundus oculi image processing device 10 shown in FIG. 1 is omitted, and only a different portion, namely, a motion vector detection portion 100 that differs from the motion vector detection portion 32 of the fundus oculi image processing device 10 shown in FIG. 1, will be explained.

Configuration Example and Processing of Motion Vector Detection Portion 100

Figure 9:
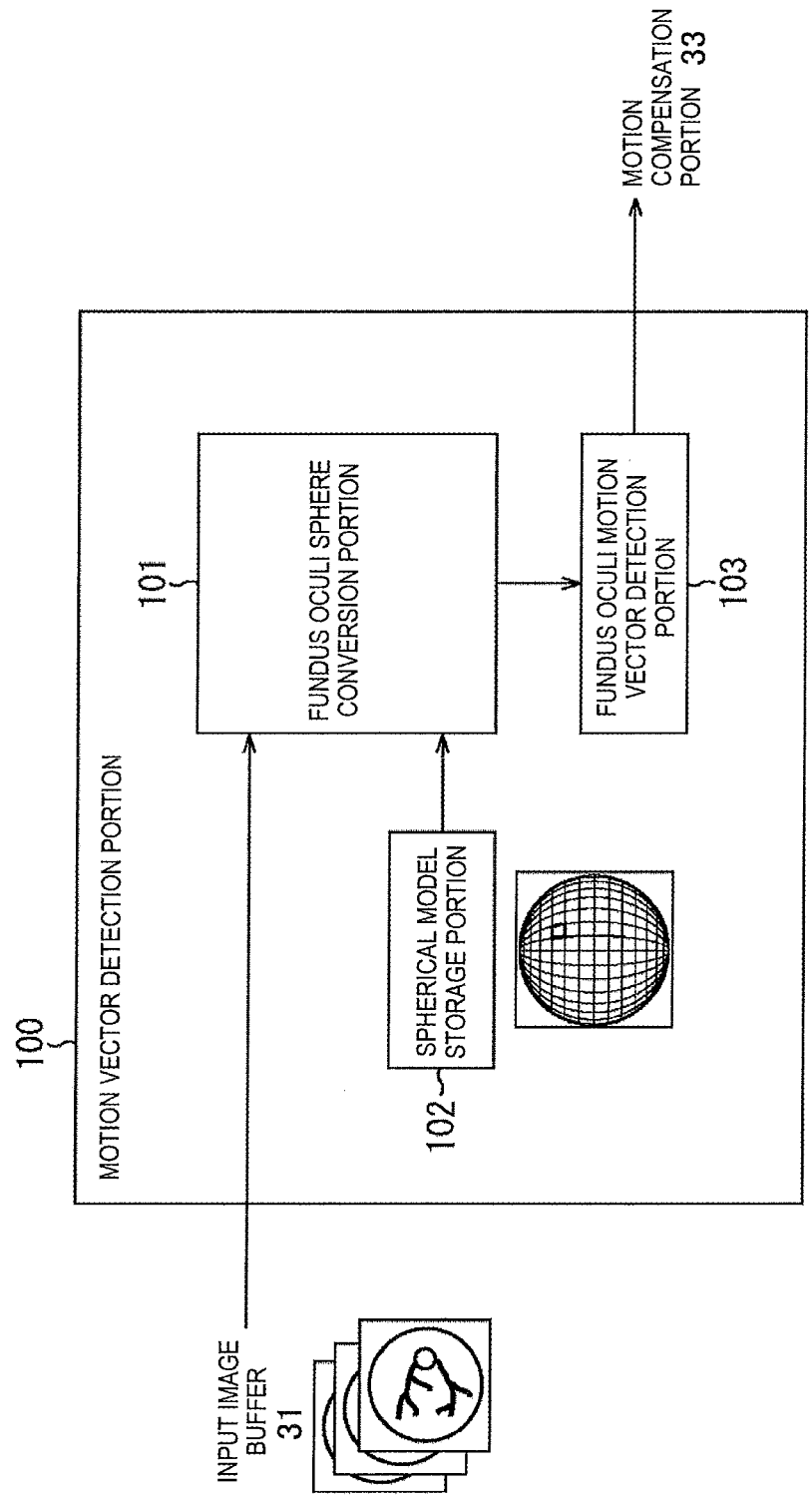
FIG. 9 is a block diagram showing a configuration example of a motion vector detection portion.
Figure 10:
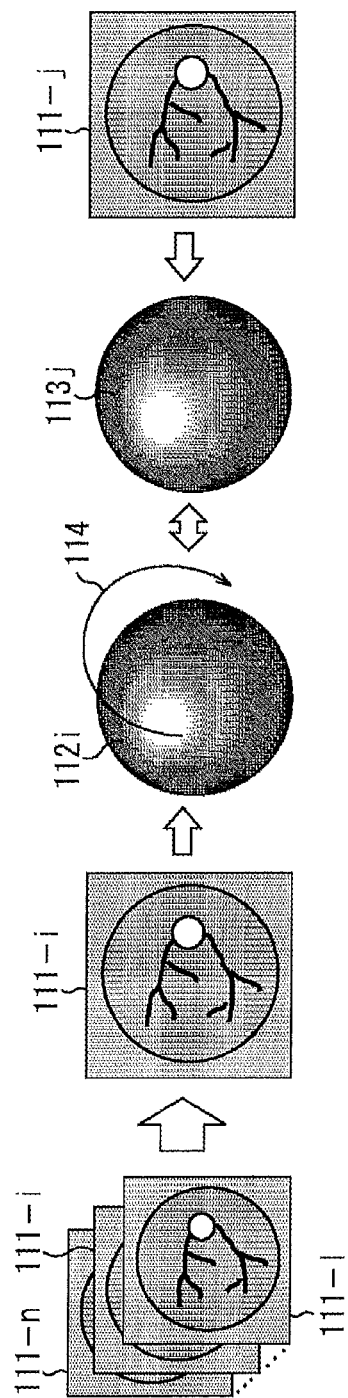
FIG. 10 is a diagram illustrating specific processing of the motion vector detection portion.

FIG. 9 is a block diagram showing a configuration example of the motion vector detection portion 100. FIG. 10 is a diagram illustrating specific processing of the motion vector detection portion 100.

As shown in FIG. 9, the motion vector detection portion 100 includes a fundus oculi sphere conversion portion 101, a spherical model storage portion 102 and a fundus oculi motion vector detection portion 103.

The fundus oculi sphere conversion portion 101 reads out data of a processing target fundus oculi image 111-$i$ and data of a comparison target fundus oculi image 111-$j$ that is different from the processing target, from among respective data of n sheets of fundus oculi images 111-$l$ to 111-$n$ that are respectively held as input image data in the input image buffer 31, as shown in FIG. 10. Here, n is an integer equal to or larger than 2 and indicates a total number of the input images held in the input image buffer 31. i is an integer equal to or larger than 1 and equal to or smaller than n−1. j is an integer equal to or larger than 1 and equal to or smaller than n, and is an integer different from the integer i. For example, in the present embodiment, j=i+1 is set.

As shown in FIG. 10, the fundus oculi sphere conversion portion 101 applies the whole of the processing target fundus oculi image 111-$i$ to a spherical model that is stored in the spherical model storage portion 102. Thus, the processing target fundus oculi image 111-$i$ is converted into a fundus oculi image 112$i$ on the spherical model. Note that the converted fundus oculi image 112$i$ is hereinafter referred to as the processing target spherical fundus oculi image 112$i$.

The fundus oculi sphere conversion portion 101 also applies a comparison target fundus oculi image 111-$j$ to the spherical model stored in the spherical model storage portion 102, in a similar manner to the above. By doing this, the comparison target fundus oculi image 111-$j$ is converted into a fundus oculi image 113$j$ on the spherical model. Note that the converted fundus oculi image 113$j$ is hereinafter referred to as the comparison target spherical fundus oculi image 113$j$.

The fundus oculi motion vector detection portion 103 repeatedly calculates a degree of similarity while rotating the processing target spherical fundus oculi image 112$i$ and the comparison target spherical fundus oculi image 113$j$. In summary, matching is performed on the whole sphere. Here, a technique for matching between the processing target spherical fundus oculi image 112$i$ and the comparison target spherical fundus oculi image 113$j$ is not particularly limited.

The fundus oculi motion vector detection portion 103 detects a motion vector 114 of the whole fundus oculi, based on a positional relationship between the processing target spherical fundus oculi image 112$i$ and the comparison target spherical fundus oculi image 113$j$ matched (namely, having a highest degree of similarity) with the processing target spherical fundus oculi image 112$i$. The fundus oculi motion vector detection portion 103 supplies, to the motion compensation portion 33, the motion vector 114 of the whole fundus oculi in the processing target spherical fundus oculi image 112$i$.

Thus, motion compensation using the motion vector 114 of the whole fundus oculi is performed on the data of the processing target fundus oculi image 111-$i$ by the motion compensation portion 33, as described above with reference to FIG. 1.

Next, an explanation will be given of fundus oculi image generation processing of the fundus oculi image processing device 10 according to the third embodiment that has the motion vector detection portion 100 configured in this manner. The fundus oculi image generation processing according to the third embodiment is performed in accordance with the flowchart shown in FIG. 4, in a similar manner to the first embodiment. However, content of motion vector detection processing at step S13 in the third embodiment is different from that in the first embodiment. Therefore, hereinafter, the motion vector detection processing at step S13 in the third embodiment will be explained with reference to FIG. 11.

Flow of Motion Vector Detection Processing

Figure 11:
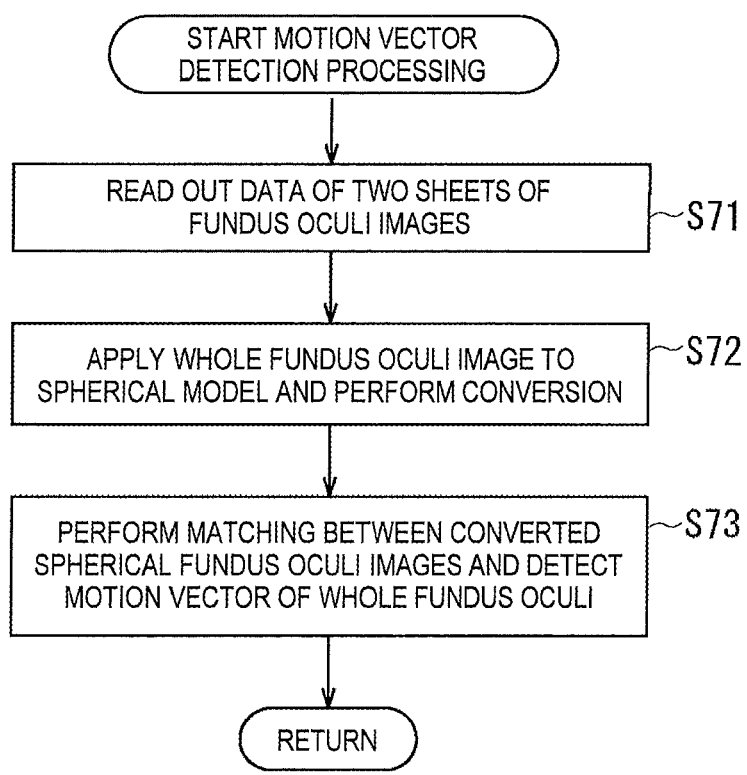
FIG. 11 is a flowchart illustrating a flow of motion vector detection processing.

FIG. 11 is a flowchart illustrating a flow of the motion vector detection processing.

At step S71, the fundus oculi sphere conversion portion 101 reads out data of two sheets of fundus oculi images, which are the processing target and the comparison target, from the input image buffer 31.

At step S72, the fundus oculi sphere conversion portion 101 applies the processing target whole fundus oculi image and the comparison target whole fundus oculi image read out at step S71 to the spherical model stored in the spherical model storage portion 102. The fundus oculi sphere conversion portion 101 converts them to spherical fundus oculi images, respectively.

At step S73, the fundus oculi motion vector detection portion 103 performs matching between the converted processing target spherical fundus oculi image and the converted comparison target spherical fundus oculi image, and detects a motion vector of the whole fundus oculi.

This completes the motion vector detection processing.

In the present embodiment, matching is performed after the processing target whole fundus oculi image and the comparison target whole fundus oculi image have each been applied to the spherical model. Therefore, the whole fundus oculi images on the spherical model are used in the degree of similarity calculation between the processing target fundus oculi image and the comparison target fundus oculi image. Thus, the motion vector of the whole fundus oculi, which is a substantially spherical body, can be detected accurately. Since the image processing using this motion vector is performed on the captured fundus oculi images, a fundus oculi image with higher image quality is generated in comparison with the second embodiment.

Fourth Embodiment

In the fundus oculi image processing devices 10 according to the first to third embodiments, the motion vector of the whole fundus oculi is detected by performing matching between the processing target fundus oculi image and the comparison target fundus oculi image. However, in many cases, the fundus oculi image basically has a substantially uniform color in the whole image. Further, since the amount of irradiated light is reduced, the fundus oculi image tends to be a relatively dark image. In addition, a plurality of times of image capture by the imaging portion 21 is performed in a relatively short time and under conditions that are as close to each other as possible. Therefore, an amount of motion between the plurality of fundus oculi images tends to be relatively small. Furthermore, even when there is a motion, it is rare that some regions of the fundus oculi image show a significantly large movement compared to the other regions, and substantially the whole image tends to move almost uniformly. Accordingly, detection of the motion vector may become difficult. To address this, instead of detecting the motion vector, alignment of the fundus oculi image may be performed using biological information of the photographic subject, with respect to the whole fundus oculi image.

In the present embodiment, for example, information of a blood vessel shape is used as the biological information of the photographic subject that is used for alignment of the fundus oculi image. Note that the biological information of the photographic subject is not limited to this example, and it may be any information. For example, information of the shape of a nerve, a nerve papilla or the like may be adopted as the biological information of the photographic subject. Further, when an organ or a cell is used as the photographic subject, information of the shape etc. of the cell or a nucleus of the cell may be adopted as the biological information of the photographic subject. Furthermore, a plurality of types of biological information (for example, a blood vessel and an optic papilla etc.) may be combined and adopted.

Configuration Example and Processing of Fundus Oculi Image Processing Device

Figure 12:
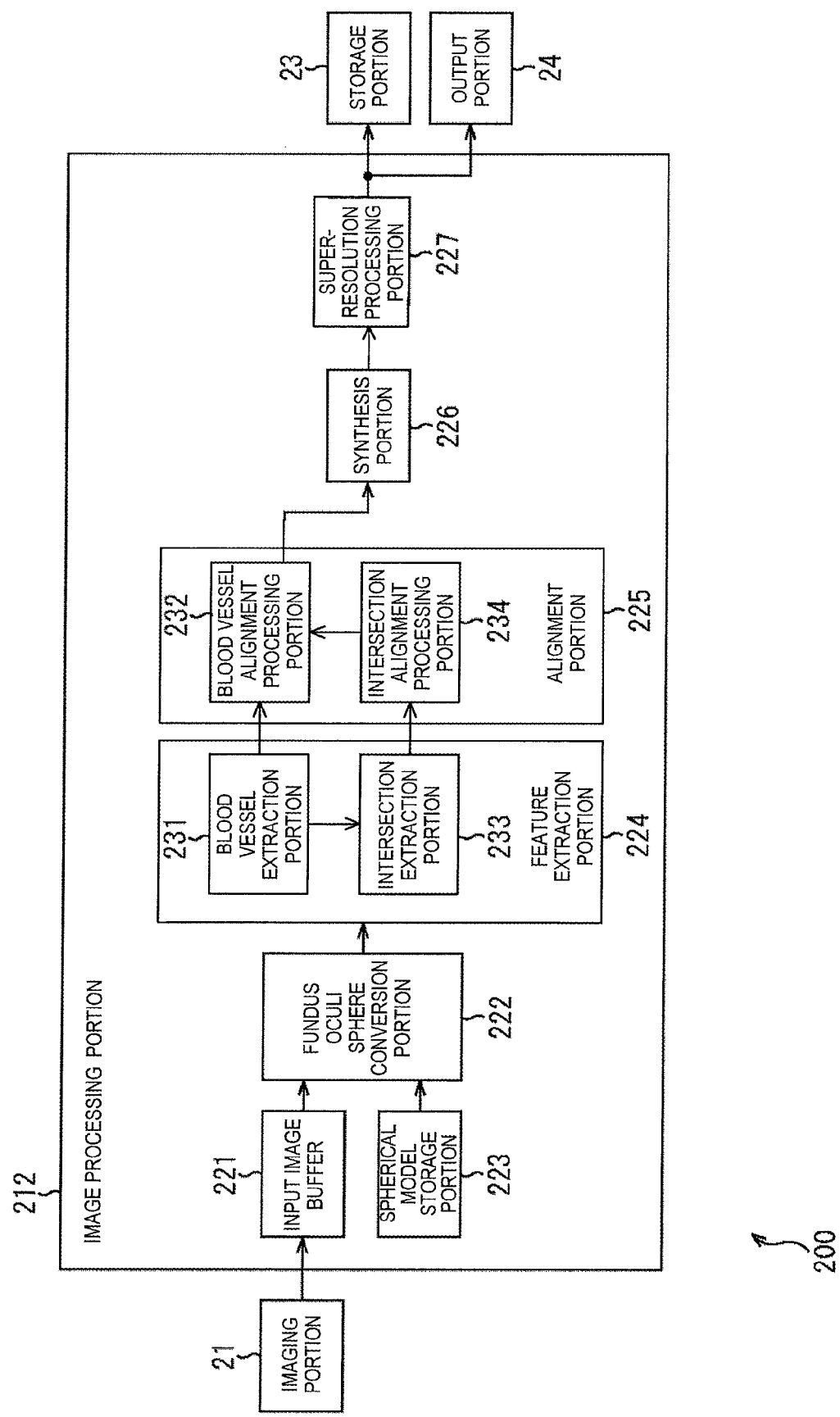
FIG. 12 is a block diagram showing a configuration example of a fundus oculi image processing device.

FIG. 12 is a block diagram showing a configuration example of a fundus oculi image processing device 200.

The fundus oculi image processing device 200 shown in FIG. 12 has basically the same function and configuration as those of the fundus oculi image processing device 10 shown in FIG. 1. Therefore, hereinafter, an explanation of same portions as those of the fundus oculi image processing device 10 shown in FIG. 1 is omitted, and only a different portion, namely, an image processing portion 212 that differs from the image processing portion 22 of the fundus oculi image processing device 10 shown in FIG. 1, will be explained.

The image processing portion 212 includes an input image buffer 221, a fundus oculi sphere conversion portion 222, a spherical model storage portion 223, a feature extraction portion 224, an alignment portion 225, a synthesis portion 226 and a super-resolution processing portion 227.

The input image buffer 221 has basically the same function and configuration as those of the input image buffer 31 shown in FIG. 1. The input image buffer 221 holds data of fundus oculi images with low image quality that are sequentially supplied from the imaging portion 21, as respective data of the input images. The data of each of the input images is read out from the input image buffer 221 at a predetermined timing and is supplied to the fundus oculi sphere conversion portion 222.

The fundus oculi sphere conversion portion 222 has basically the same function and configuration as those of the fundus oculi sphere conversion portion 101 shown in FIG. 9. The fundus oculi sphere conversion portion 222 reads out data of a processing target fundus oculi image and data of a comparison target fundus oculi image that is different from the processing target, from among respective data of a plurality of fundus oculi images that are respectively held as input image data in the input image buffer 221. Then, the fundus oculi sphere conversion portion 222 applies the processing target fundus oculi image and the comparison target fundus oculi image to a spherical model that is stored in the spherical model storage portion 223. Thus, the processing target fundus oculi image and the comparison target fundus oculi image are converted into fundus oculi images on the spherical model. Note that the converted processing target fundus oculi image is hereinafter referred to as a processing target spherical fundus oculi image. Further, the converted comparison target fundus oculi image is hereinafter referred to as a comparison target spherical fundus oculi image. The fundus oculi sphere conversion portion 222 supplies the processing target spherical fundus oculi image and the comparison target spherical fundus oculi image to the feature extraction portion 224.

The feature extraction portion 224 includes a blood vessel extraction portion 231 and an intersection extraction portion 233. The alignment portion 225 includes a blood vessel alignment processing portion 232 and an intersection alignment processing portion 234. Specific processing of the feature extraction portion 224 and the alignment portion 225 will be explained with reference to FIG. 13.

Figure 13:
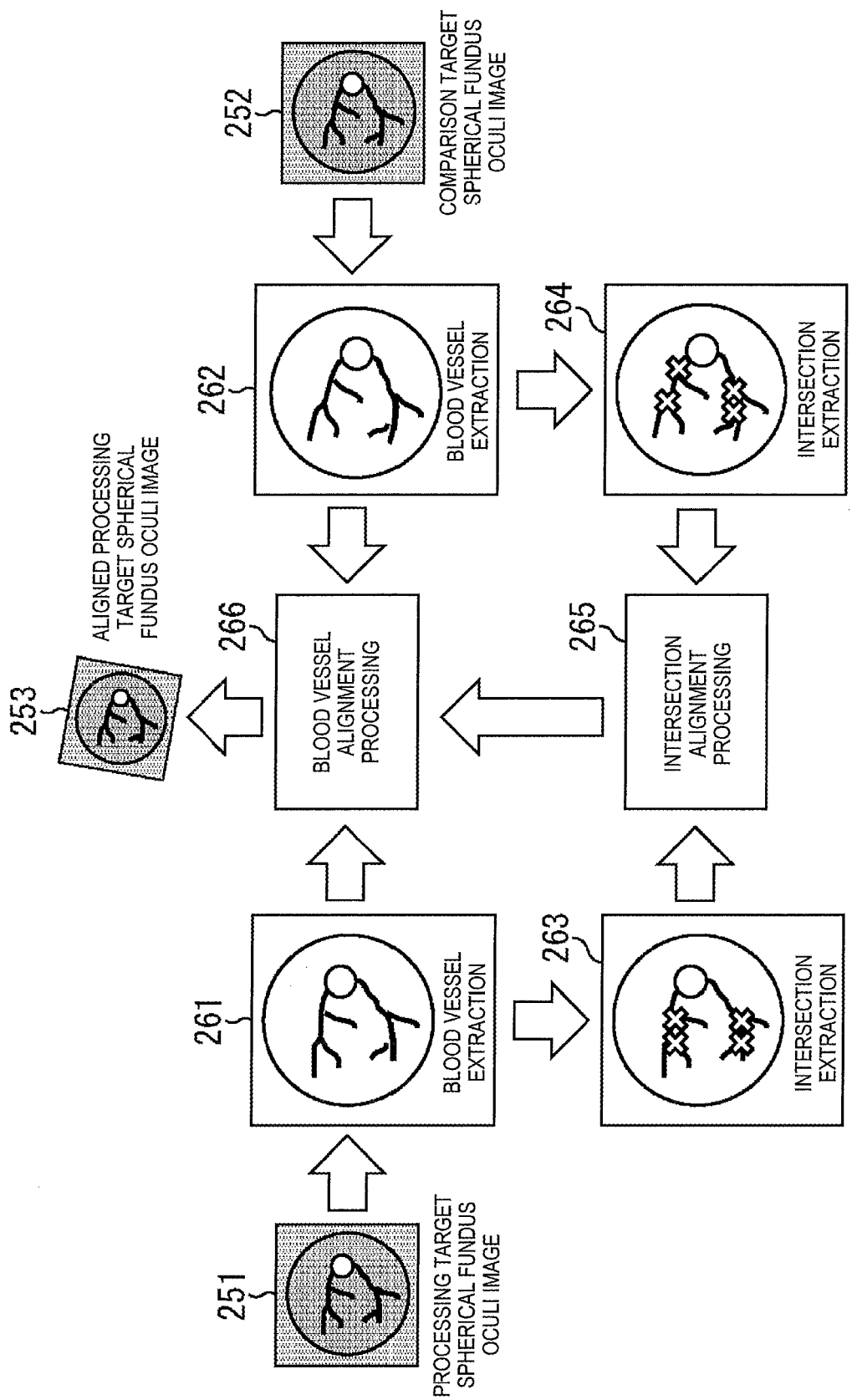
FIG. 13 is a diagram illustrating specific processing of a feature extraction portion and an alignment portion.

As shown in FIG. 13, the blood vessel extraction portion 231 extracts features (processing 261, 262), such as the shape and position etc., of a blood vessel, from each of a processing target spherical fundus oculi image 251 and a comparison target spherical fundus oculi image 252 supplied from the fundus oculi sphere conversion portion 222. At this time, the blood vessel extraction portion 231 uses an R component of RGB components to extract a blood vessel from each of the processing target spherical fundus oculi image 251 and the comparison target spherical fundus oculi image 252, as in a method described in "Fundus oculi image synthesis method using blood vessel features", Katsuyoshi Tanabe, Tetsuro Tsubouchi, Hidenori Okuda, Masahiro Oku, 2007. The blood vessel extraction portion 231 supplies the features, such as the shape and position etc., of the blood vessel extracted from each of the processing target spherical fundus oculi image 251 and the comparison target spherical fundus oculi image 252 to the blood vessel alignment processing portion 232, as a blood vessel extraction result of each of the images.

As shown in FIG. 13, the blood vessel alignment processing portion 232 performs blood vessel alignment processing (processing 266) between the processing target spherical fundus oculi image 251 and the comparison target spherical fundus oculi image 252, using the blood vessel extraction result of the processing target spherical fundus oculi image 251 and the blood vessel extraction result of the comparison target spherical fundus oculi image 252 that are supplied from the blood vessel extraction portion 231.

The blood vessel alignment processing portion 232 supplies the synthesis portion 226 with a processing target spherical fundus oculi image 253 on which the blood vessel alignment processing has been performed. Note that the configuration and processing of the blood vessel alignment processing portion 232 will be explained in more detail later with reference to FIG. 14 and FIG. 15.

Further, before the blood vessel alignment processing (the processing 266) is performed using the blood vessel extraction results, simple alignment may be performed using positions of blood vessel intersections. Note that the blood vessel intersection is a portion at which blood vessels intersect (including a case of a torsion position in actuality) in the fundus oculi image, or a portion at which the blood vessels diverge.

In this case, as shown in FIG. 13, the blood vessel extraction portion 231 supplies a blood vessel extraction result of the processing target spherical fundus oculi image 251 that is obtained by the processing 261, to the intersection extraction portion 233. Further, as shown in FIG. 13, the blood vessel extraction portion 231 supplies a blood vessel extraction result of the comparison target spherical fundus oculi image 252 that is obtained by the processing 262, to the intersection extraction portion 233.

As shown in FIG. 13, the intersection extraction portion 233 extracts an intersection (processing 263) using the blood vessel extraction result of the processing target spherical fundus oculi image 251 that is supplied from the blood vessel extraction portion 231. Further, the intersection extraction portion 233 extracts an intersection (processing 264) using the blood vessel extraction result of the comparison target spherical fundus oculi image 252 that is supplied from the blood vessel extraction portion 231. The intersection extraction portion 233 supplies positions of the intersections respectively extracted from the processing target spherical fundus oculi image 251 and the comparison target spherical fundus oculi image 252 to the intersection alignment processing portion 234, as intersection extraction results.

As shown in FIG. 13, the intersection alignment processing portion 234 performs intersection alignment processing (processing 265) between the processing target spherical fundus oculi image 251 and the comparison target spherical fundus oculi image 252, using the respective intersection extraction results of the processing target spherical fundus oculi image 251 and the comparison target spherical fundus oculi image 252 that are supplied from the intersection extraction portion 233. The intersection alignment processing portion 234 supplies a result of the intersection alignment processing to the blood vessel alignment processing portion 232, as an intersection alignment result.

The blood vessel alignment processing portion 232 uses the intersection alignment result supplied from the intersection alignment processing portion 234 as a spherical fundus oculi image in an initial state, and further performs blood vessel alignment processing (processing 266) using the blood vessel extraction results on the spherical fundus oculi image in the initial state. More specifically, while performing alignment in a similar manner to the intersection alignment in accordance with the intersection alignment result, the blood vessel alignment processing portion 232 superimposes the respective blood vessel extraction results and sets the superimposed image as the initial state.

In this manner, the blood vessel alignment processing portion 232 can further perform alignment using the blood vessel extraction results on the spherical fundus oculi image for which alignment has been simply performed using the intersection. Therefore, the blood vessel alignment processing portion 232 can perform alignment more easily and at a higher speed.

Note that, further, alignment using other biological information may be adopted at the same time. For example, firstly, while performing alignment at a position of the optic papilla, alignment using the intersection may be further performed on the spherical fundus oculi image in the initial state, using the spherical fundus oculi image obtained by superimposing the processing target spherical fundus oculi image 251 and the comparison target spherical fundus oculi image 252 as the spherical fundus oculi image in the initial state.

When all the data of the plurality of spherical fundus oculi images that have been aligned are supplied from the blood vessel alignment processing portion 232, the synthesis portion 226 synthesizes the respective data of the plurality of spherical fundus oculi images and thereby generates data of one sheet of a fundus oculi image. The synthesis portion 226 supplies the generated data to the super-resolution processing portion 227.

The super-resolution processing portion 227 performs super-resolution processing on the data of the fundus oculi image synthesized by the synthesis portion 226, and thereby generates data of the fundus oculi image with an even higher resolution than that at the time of synthesis. The data of the high-resolution fundus oculi image generated in this manner by the super-resolution processing portion 227 is stored in the storage portion 23 or output from the output portion 24.

Next, the configuration and processing of the blood vessel alignment processing portion 232 will be explained in detail.

Figure 14:
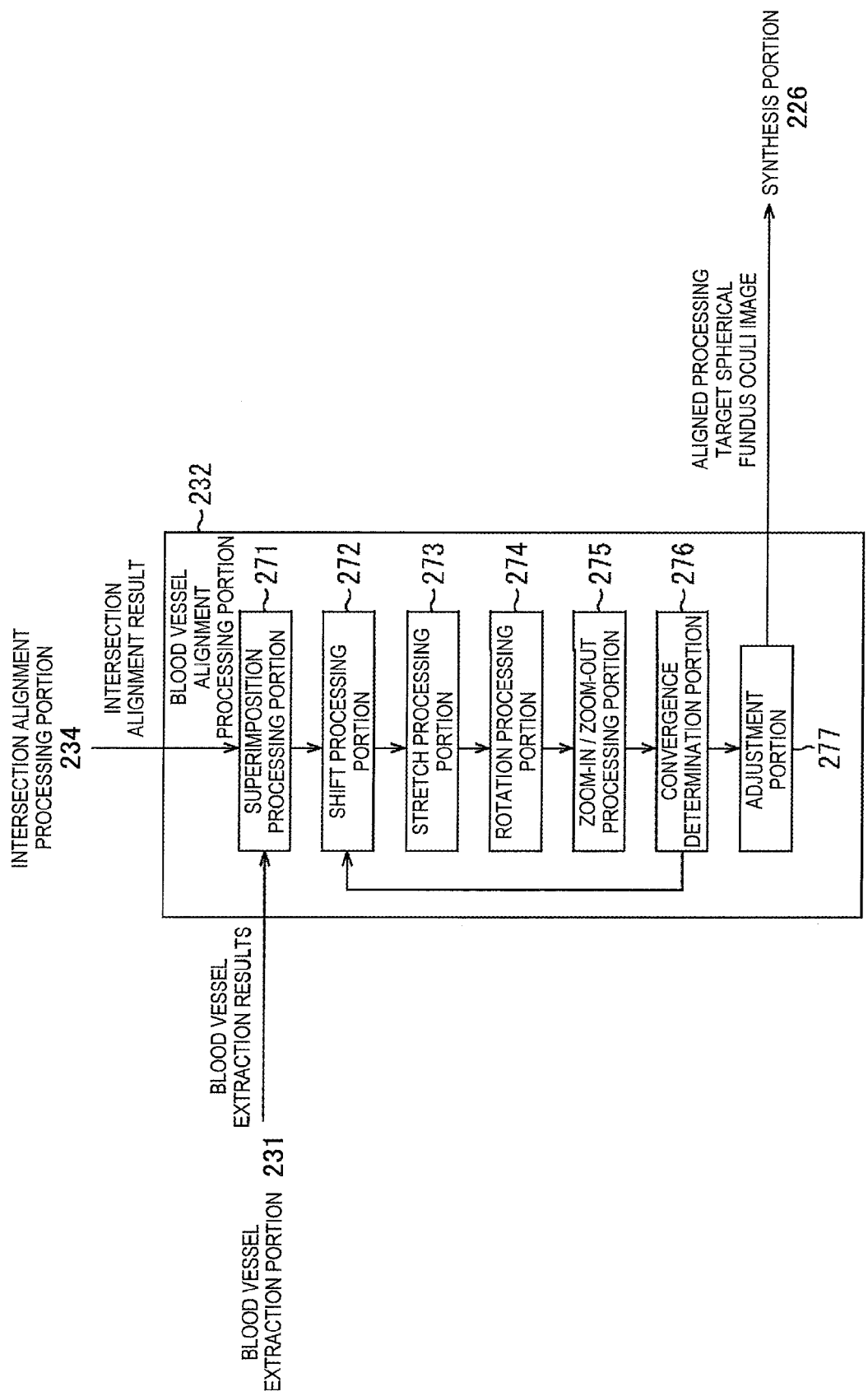
FIG. 14 is a diagram showing a configuration example of a blood vessel alignment processing portion.
Figure 15:
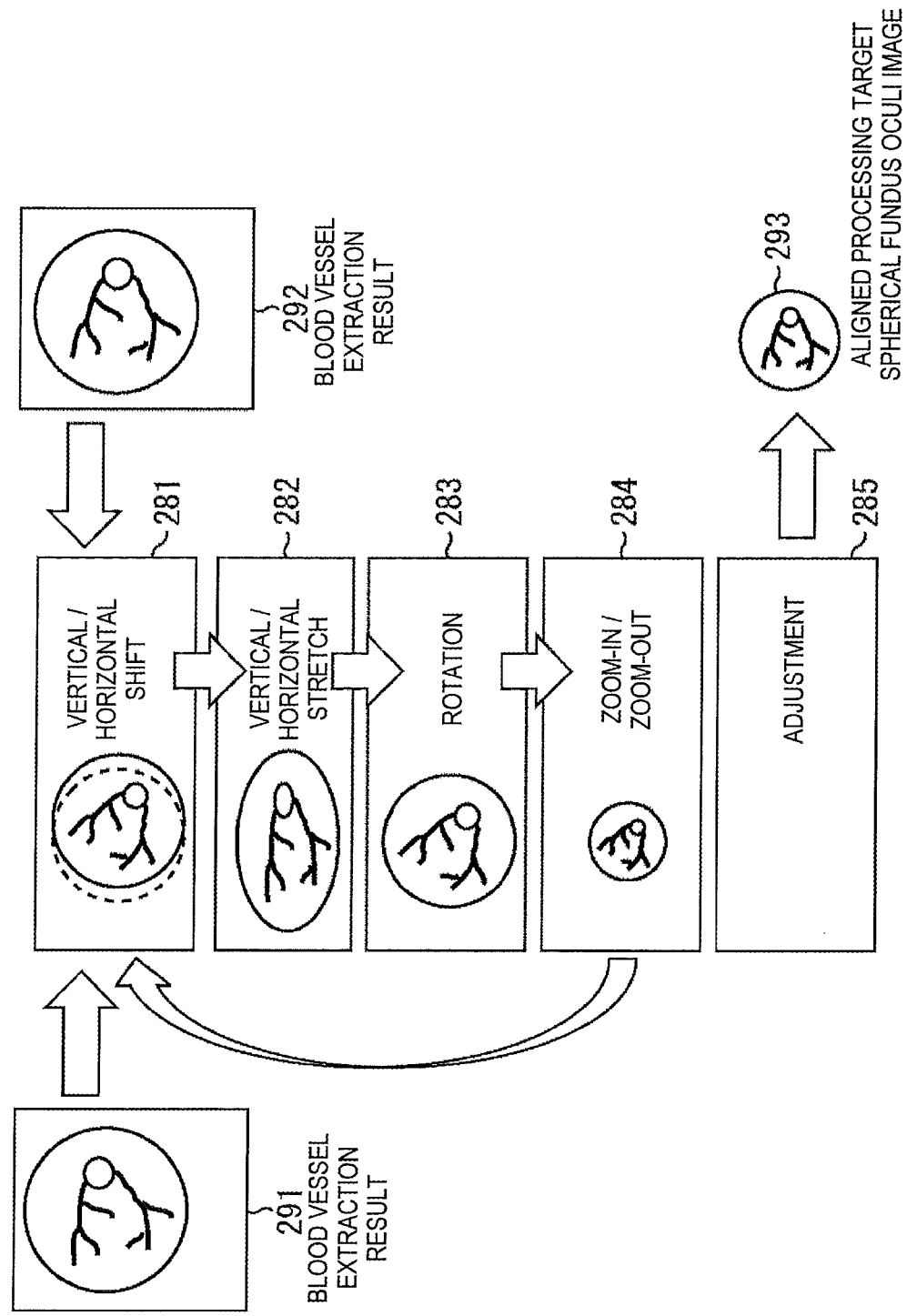
FIG. 15 is a diagram illustrating specific processing of the blood vessel alignment processing portion.

Configuration Example and Processing of Blood Vessel Alignment Processing Portion FIG. 14 is a diagram showing a configuration example of the blood vessel alignment processing portion 232. FIG. 15 is a diagram illustrating specific processing of the blood vessel alignment processing portion 232.

As shown in FIG. 14, the blood vessel alignment processing portion 232 includes a superimposition processing portion 271, a shift processing portion 272, a stretch processing portion 273, a rotation processing portion 274, a zoom-in/zoom-out processing portion 275, a convergence determination portion 276 and an adjustment portion 277.

The superimposition processing portion 271 superimposes the respective blood vessel extraction results of the processing target spherical fundus oculi image 251 and the comparison target spherical fundus oculi image 252 that are supplied from the blood vessel extraction portion 231. When alignment using the intersection is performed, the superimposition processing portion 271 superimposes the respective blood vessel extraction results while performing alignment in a similar manner to the intersection alignment using the intersection alignment result supplied from the intersection alignment processing portion 234. The superimposition processing portion 271 supplies a superimposed result to the shift processing portion 272. Note that the blood vessel alignment processing portion 232 performs alignment so that a blood vessel extraction result 292 approaches a blood vessel extraction result 291.

As shown in FIG. 15, the shift processing portion 272 performs a vertical/horizontal shift 281 that causes the whole of the blood vessel extraction result 292 to move (shift) in a given direction, such as a vertical direction or a horizontal direction. The shift processing portion 272 supplies a superimposed result to the stretch processing portion 273 in a state in which the blood vessel extraction result 292 approaches the blood vessel extraction result 291 to a maximum extent. Although any method can be used to determine how close the blood vessel extraction result 291 and the blood vessel extraction result 292 are to each other, a difference between absolute values of the two images, for example, can be used for determination. More specifically, the shift processing portion 272 causes the whole of the blood vessel extraction result 292 to move (shift) and searches for a position at which the difference between the absolute values of the blood vessel extraction result 291 and the blood vessel extraction result 292 is minimum. This determination method also applies to the following processing portions.

As shown in FIG. 15, the stretch processing portion 273 performs a vertical/horizontal stretch 282 that stretches (deforms) the blood vessel extraction result 291 in a given direction, such as the vertical direction or the horizontal direction. The stretch processing portion 273 supplies a superimposed result to the rotation processing portion 274 in a state in which the blood vessel extraction result 292 approaches the blood vessel extraction result 291 to a maximum extent. For example, the stretch processing portion 273 stretches (deforms) the blood vessel extraction result 292 in a given direction, and searches for a shape that causes the difference between the absolute values of the blood vessel extraction result 291 and the blood vessel extraction result 292 to be minimum.

As shown in FIG. 15, the rotation processing portion 274 performs a rotation 283 that rotates the blood vessel extraction result 292 in left and right directions, and supplies a superimposed result to the zoom-in/zoom-out processing portion 275 in a state in which the blood vessel extraction result 292 approaches the blood vessel extraction result 291 to a maximum extent. For example, the rotation processing portion 274 rotates the blood vessel extraction result 292 in the left and right directions, and searches for a direction in which the difference between the absolute values of the blood vessel extraction result 291 and the blood vessel extraction result 292 is minimum.

As shown in FIG. 15, the zoom-in/zoom-out processing portion 275 performs a zoom-in/zoom-out 284 that zooms in or zooms out the blood vessel extraction result 292, and supplies a superimposed result to the convergence determination portion 276 in a state in which the blood vessel extraction result 292 approaches the blood vessel extraction result 291 to a maximum extent. For example, the zoom-in/zoom-out processing portion 275 zooms in or zooms out the blood vessel extraction result 292, and searches for a size that causes the difference between the absolute values of the blood vessel extraction result 291 and the blood vessel extraction result 292 to be minimum.

The convergence determination portion 276 determines whether or not the alignment has converged, based on the supplied superimposed result. For example, the convergence determination portion 276 causes each of the above-described processing to be repeatedly performed, and compares an alignment result obtained this time with an alignment result of the previous time. When the blood vessel extraction result 292 is closer to the blood vessel extraction result 291 than the previous time, the convergence determination portion 276 determines that the alignment has not converged. When the blood vessel extraction result 292 is not closer to the blood vessel extraction result 291 than the previous time (for example, when the difference between the absolute values of the blood vessel extraction result 291 and the blood vessel extraction result 292 is not smaller than the previous time), the convergence determination portion 276 determines that the alignment has converged.

When it is determined that the alignment has not converged (for example, when the difference between the absolute values of the blood vessel extraction result 291 and the blood vessel extraction result 292 is smaller than the previous time), the convergence determination portion 276 returns the superimposed result to the shift processing portion 272 and causes the alignment to be performed again.

When it is determined that the alignment has converged, the adjustment portion 277 performs adjustment of the alignment based on cumulative convergence results obtained until the previous time. For example, it is assumed that first to fifth fundus oculi images, which are in a time ascending order, are obtained by performing image capture five times consecutively. In this case, when the fifth fundus oculi image is set as the processing target, the fourth fundus oculi image is used as the comparison target. Note that the convergence result is a result of performing alignment such that the fifth fundus oculi image approaches the fourth fundus oculi image. In summary, at a stage when the convergence is complete, the fifth fundus oculi image has only approached the fourth fundus oculi image. However, in the synthesis portion 266 that will be described later, an image (an aligned image) obtained by causing the fifth fundus oculi image to approach the first fundus oculi image is used as a synthesis target. Therefore, it is necessary to cause the image immediately after the convergence, namely, the image (the aligned image) obtained by causing the fifth fundus oculi image to approach the fourth fundus oculi image, to further approach the first fundus oculi image (namely, it is necessary to adjust the alignment).

In order to cause the fourth fundus oculi image to approach the first fundus oculi image (namely, in order to perform adjustment of the alignment), it is necessary to use the cumulative convergence results obtained until the previous time. Specifically, adjustment of the alignment to cause the fourth fundus oculi image to approach the first fundus oculi image is performed by cumulatively using a convergence result (a last convergence result) obtained by causing the fifth fundus oculi image to approach the fourth fundus oculi image, a convergence result (a second last convergence result) obtained by causing the fourth fundus oculi image to approach the third fundus oculi image, a convergence result (a third last convergence result) obtained by causing the third fundus oculi image to approach the second fundus oculi image, and a convergence result (a fourth last convergence result) obtained by causing the second fundus oculi image to approach the first fundus oculi image. Note that the order of adjustment of the alignment is not limited to this example. Conversely, adjustment of the alignment may be performed to approach a plurality of fundus oculi images to the fifth fundus oculi image. The adjustment portion 277 supplies the synthesis portion 226 with a processing target spherical fundus oculi image 293 that has been aligned.

Note that, in the above explanation, as a specific example of the alignment, four processing steps, i.e., the vertical/horizontal shift 281, the vertical/horizontal stretch 282, the rotation 283 and the zoom-in/zoom-out 284, are performed in this order. However, this is merely an example and a processing step other than the above-described processing steps may be further performed, or a part of the above-described processing steps may be omitted. Further when a plurality of processing steps are performed as described above, the processing order can be set as desired.

Further, the feature extraction portion 224 and the alignment portion 225 may perform alignment using a histogram of an edge portion, as described in, for example, "Shape Matching and Object Recognition Using Shape Contexts", Serge Belongie, Jitendra Malik, Jan Puzicha, 2002.

Further, any method can be used to determine whether or not the alignment has converged, and a method other than that described above may be used. For example, it may be determined that the alignment has converged when the difference between the absolute values of the blood vessel extraction result 291 and the blood vessel extraction result 292 is equal to or smaller than a predetermined threshold value.

Note that the alignment using the intersection of blood vessels is also performed basically in the same manner as the alignment using the whole blood vessels. In other words, the intersection alignment processing portion 234 has basically the same configuration as the blood vessel alignment processing portion 232, and basically performs the same processing, the only difference being whether the biological information used to perform alignment is the shape of the whole blood vessels or the intersection of the blood vessels.

As described above, since the fundus oculi image is an image of a living organism, the fundus oculi image processing device 200 makes use of features of the image and thereby performs alignment in the whole image using the biological information included in the fundus oculi image. By doing this, the fundus oculi image processing device 200 can achieve more accurate alignment more easily.

The configuration of the fundus oculi image processing device 200 is explained above with reference to FIG. 12 to FIG. 15. Next, fundus oculi image generation processing that is performed by the fundus oculi image processing device 200 configured in this manner will be explained with reference to FIG. 16.

Flow of Fundus Oculi Image Generation Processing

Figure 16:
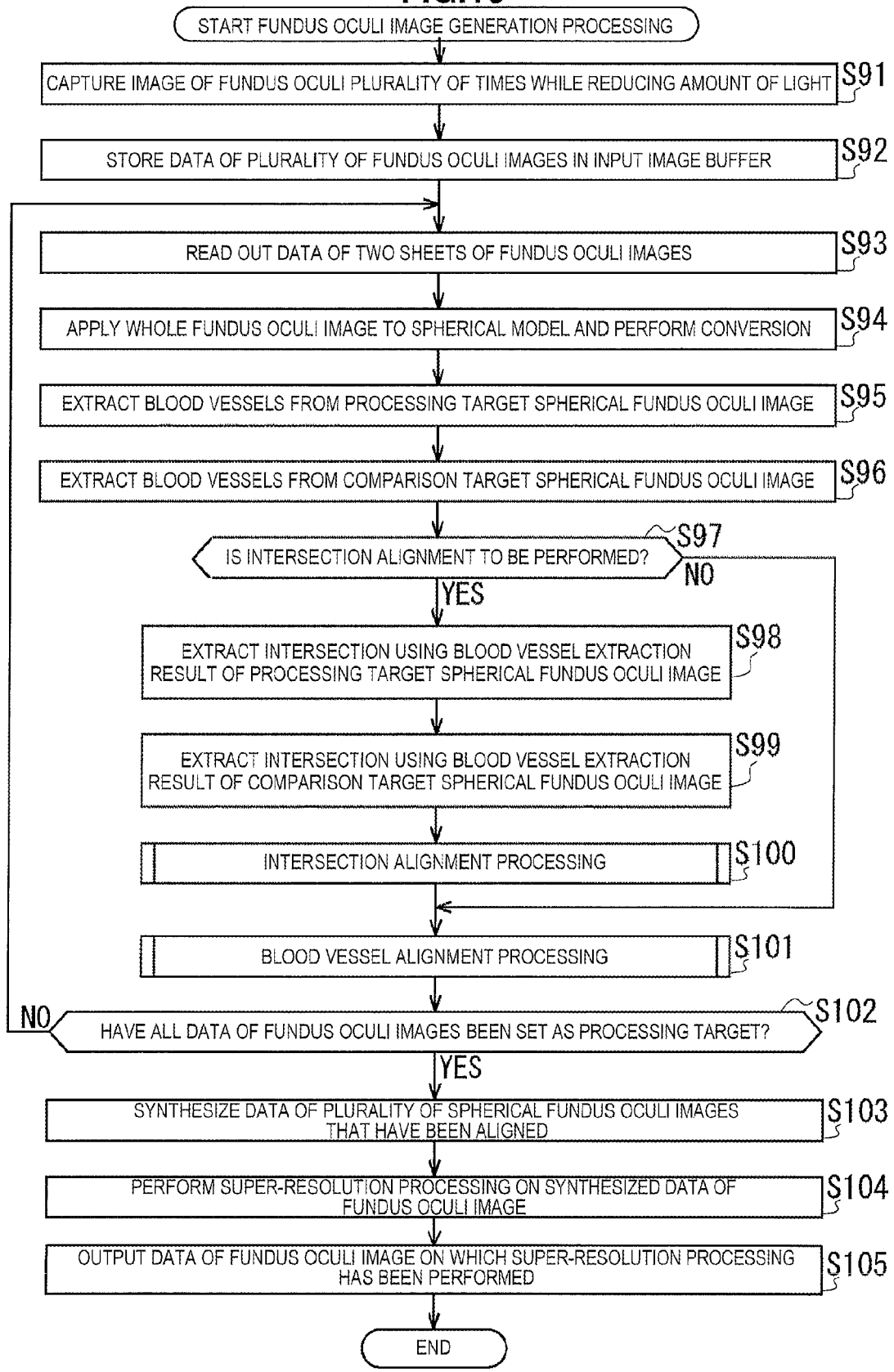
FIG. 16 is a flowchart illustrating a flow of fundus oculi image generation processing.

FIG. 16 is a flowchart illustrating a flow of the fundus oculi image generation processing.

At step S91, the imaging portion 21 reduces the amount of light and captures an image of the fundus oculi of the test subject a plurality of times. Note that, as described above, image capture of the fundus oculi by the imaging portion 21 may be performed a plurality of times to obtain still images or may be performed once to obtain moving images.

At step S92, the image processing portion 212 causes the input image buffer 221 to store data of the plurality of fundus oculi images with low image quality obtained by the processing at step S91.

At step S93, the fundus oculi sphere conversion portion 222 reads out data of two sheets of fundus oculi images, which are a processing target and a comparison target, from the input image buffer 221.

At step S94, the fundus oculi sphere conversion portion 222 applies the whole processing target fundus oculi image and the whole comparison target fundus oculi image that are read out at step S93 to the spherical model stored in the spherical model storage portion 223, and converts them into a processing target spherical fundus oculi image and a comparison target spherical fundus oculi image, respectively.

At step S95, the blood vessel extraction portion 231 extracts the shape and position of the blood vessels from the processing target spherical fundus oculi image. The extracted shape and position of the blood vessels are supplied to the blood vessel alignment processing portion 232 as a blood vessel extraction result.

At step S96, the blood vessel extraction portion 231 extracts the shape and position of the blood vessels from the comparison target spherical fundus oculi image. The extracted shape and position of the blood vessels are supplied to the blood vessel alignment processing portion 232 as a blood vessel extraction result.

At step S97, the feature extraction portion 224 determines whether or not to perform intersection alignment.

When the intersection alignment is not to be performed, NO is determined at step S97 and the processing proceeds to step S101. Note that processing from step S101 onward will be described later.

On the other hand, when the intersection alignment is to be performed, YES is determined at step S97 and the processing proceeds to step S98. In this case, the blood vessel extraction portion 231 supplies the blood vessel extraction results extracted at step S95 and step S96 to the intersection extraction portion 233.

At step S98, the intersection extraction portion 233 extracts an intersection using the blood vessel extraction result of the processing target spherical fundus oculi image. The position of the extracted intersection is supplied to the intersection alignment processing portion 234 as an intersection extraction result.

At step S99, the intersection extraction portion 233 extracts an intersection using the blood vessel extraction result of the comparison target spherical fundus oculi image. The position of the extracted intersection is supplied to the intersection alignment processing portion 234 as an intersection extraction result.

At step S100, the intersection alignment processing portion 234 performs intersection alignment processing between the processing target spherical fundus oculi image 251 and the comparison target spherical fundus oculi image 252, using the intersection extraction results supplied at step S98 and step S99.

Note that the intersection alignment processing at step S100 is performed in the same manner as blood vessel alignment processing that will be described later with reference to FIG. 17, except that the intersection of blood vessels is used for alignment instead of the whole blood vessels. Therefore, an explanation of the intersection alignment processing at step S100 is omitted here to avoid repetition.

At step S101, the blood vessel alignment processing portion 232 performs the blood vessel alignment processing. More specifically, with respect to the spherical fundus oculi image which has been simply aligned using the intersection, the blood vessel alignment processing portion 232 further performs blood vessel alignment using the blood vessel extraction results. The blood vessel alignment processing at step S101 will be described in more detail later with reference to FIG. 17.

At step S102, the image processing portion 212 determines whether or not all the data of the fundus oculi images have been set as the processing target.

When all the data of the fundus oculi images have not yet been set as the processing target, NO is determined at step 102 and the processing is returned to step S93. Then, processing from step S93 onward is repeated. More specifically, loop processing from step S93 to step S102 is repeated until all the data of the fundus oculi images are set as the processing target.

After that, when all the data of the fundus oculi images have been set as the processing target, YES is determined at step 102 and the processing proceeds to step S103.

At step S103, the synthesis portion 226 synthesizes data of the plurality of spherical fundus oculi images that have been aligned. As a result, data of one sheet of a fundus oculi image is generated.

At step S104, the super-resolution processing portion 227 performs super-resolution processing on the synthesized data of the fundus oculi image. As a result, data of the fundus oculi image with a higher resolution than that at the time of synthesis at step S103 is generated.

At step S105, the image processing portion 212 causes the storage portion 23 to store the data of the fundus oculi image on which the super-resolution processing has been performed, or causes the output portion 24 to output the data.

This completes the fundus oculi image generation processing. Next, the blood vessel alignment processing at step S101 will be explained.

Flow of Blood Vessel Alignment Processing

Figure 17:
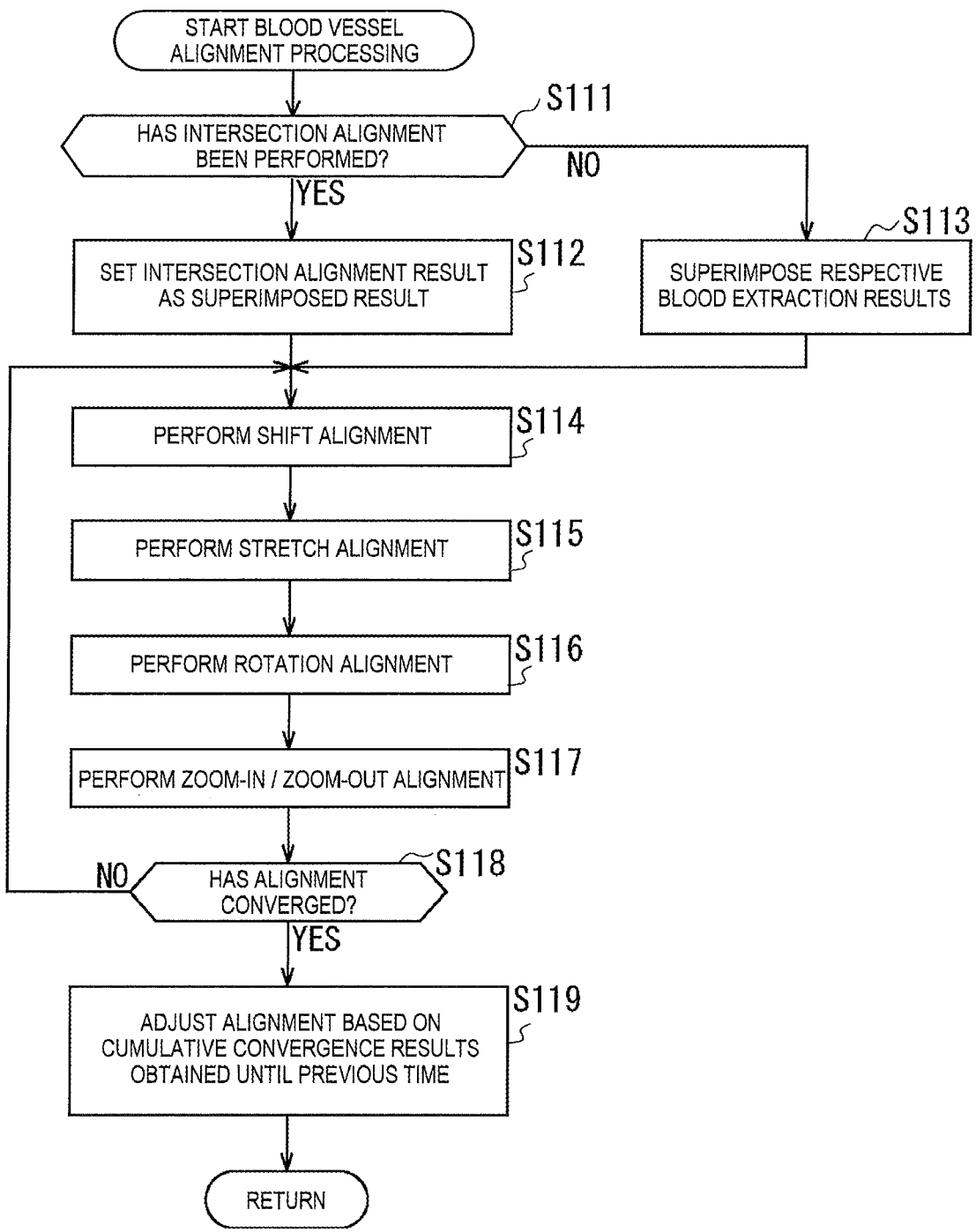
FIG. 17 is a flowchart illustrating a flow of blood vessel alignment processing.

FIG. 17 is a flowchart illustrating a flow of the blood vessel alignment processing at step S101 shown in FIG. 16.

At step S111, the superimposition processing portion 271 determines whether or not the intersection alignment has been performed.

When the intersection alignment has been performed, YES is determined at step S111 and the processing proceeds to step S112.

At step S112, the superimposition processing portion 271 sets the intersection alignment result as a superimposed result. In accordance with the superimposed result, the superimposition processing portion 271 superimposes the respective blood vessel extraction results of the processing target spherical fundus oculi image and the comparison target spherical fundus oculi image that are supplied from the blood vessel extraction portion 231.

On the other hand, when the intersection alignment has not been performed, NO is determined at step S111 and the processing proceeds to step S113.

At step S113, the superimposition processing portion 271 superimposes the respective blood vessel extraction results of the processing target spherical fundus oculi image and the comparison target spherical fundus oculi image.

At step S114, the shift processing portion 272 performs shift alignment that shifts the blood vessel extraction result of the processing target spherical fundus oculi image.

At step S115, the stretch processing portion 273 performs stretch alignment that elongates and contracts the blood vessel extraction result of the processing target spherical fundus oculi image.

At step S116, the rotation processing portion 274 performs rotation alignment that rotates the blood vessel extraction result of the processing target spherical fundus oculi image.

At step S117, the zoom-in/zoom-out processing portion 275 performs zoom-in/zoom-out alignment that zooms in or zooms out the blood vessel extraction result of the processing target spherical fundus oculi image.

At step S118, the convergence determination portion 276 determines whether or not the alignment has converged.

When the alignment has not converged, NO is determined at step S118 and the processing is returned to step S114. Then, processing from step S114 onward is repeated. More specifically, loop processing from step S114 to step S118 is repeated until the alignment converges.

After that, when the alignment has converged, YES is determined at step S118 and the processing proceeds to step S119.

At step S119, the adjustment portion 277 adjusts the alignment based on cumulative convergence results obtained until the previous time. As a result, the aligned processing target spherical fundus oculi image is output to the synthesis portion 226.

This completes the blood vessel alignment processing, and the processing proceeds to step S102 shown in FIG. 16.

In this manner, the alignment of the fundus oculi images is performed using biological information of the photographic subject. Thus, even in a situation in which it is difficult to detect a motion vector, a higher quality fundus oculi image can be obtained while reducing a burden on the test subject.

Note that the spherical model used in the above-described examples may be switched to an appropriate spherical model for each test subject in accordance with conditions of each test subject, such as an eye axis length, eyesight and the like.

Further, the fundus oculi is not a perfect sphere. Therefore, mask processing can also be performed on a region that cannot approximate a sphere using a spherical model, so that the region is not used for matching processing or alignment processing.

[Application to a Program of the Present Technology]

The series of processes described above can be executed by hardware and can also be executed by software.

Figure 18:
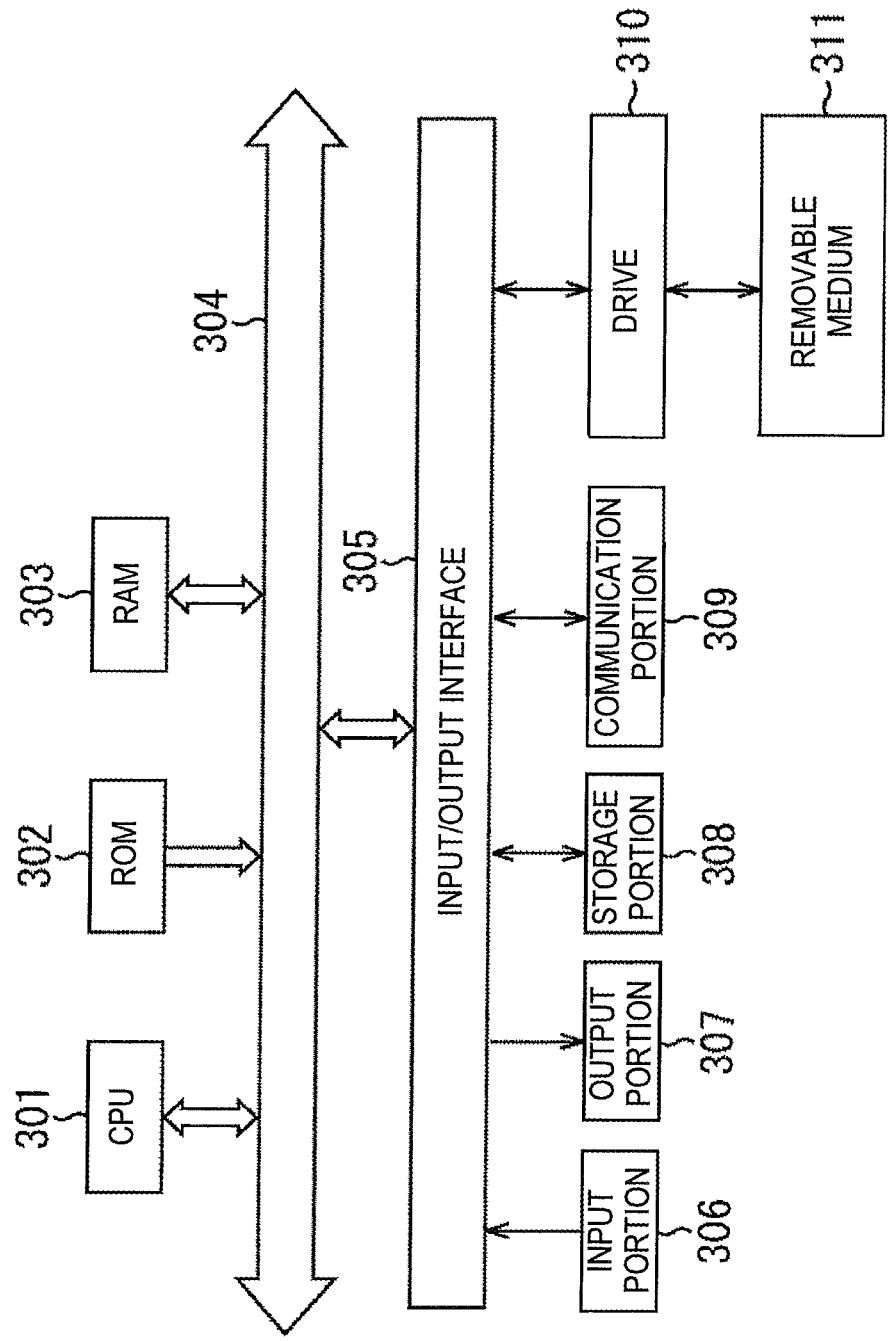
FIG. 18 is a block diagram showing a hardware configuration example of an image processing device to which the present technology is applied.

In this case, a personal computer shown in FIG. 18, for example, may be used as at least a part of the above-described image processing device.

In FIG. 18, a CPU 301 performs various types of processing in accordance with a program stored in a ROM 302. Further, the CPU 301 performs various types of processing in accordance with a program that is loaded from a storage portion 308 to a RAM 303. Data etc. that is necessary for the CPU 301 to perform the various types of processing is also stored in the RAM 303 as appropriate.

The CPU 301, the ROM 302 and the RAM 303 are mutually connected via a bus 304. An input output (I/O) interface 305 is also connected to the bus 304.

An input portion 306 that is formed by a keyboard, a mouse and the like, and an output portion 307 that is formed by a display and the like are connected to the I/O interface 305. Further, the storage portion 308 that is formed by a hard disk and the like, and a communication portion 309 that is formed by a modem, a terminal adaptor and the like are connected to the I/O interface 305. The communication portion 309 controls communication that is performed with another device (not shown in the drawings) via a network including the Internet.

Further, a drive 310 is connected to the I/O interface 305 according to need. A removable media 311 that is formed by a magnetic disk, an optical disk, a magneto optical disk, a semiconductor memory, or the like is attached as appropriate. Then, a computer program that is read from the removable media 311 is installed in the storage portion 308 according to need.

When the series of processing is performed by software, a program that forms the software is installed from a network or a recording medium to a computer that is incorporated in a dedicated hardware, or to, for example, a general-purpose personal computer that can perform various types of functions by installing various types of programs.

The recording medium that includes this type of program is not only formed by the removable media (package media) 311 that is distributed separately from a main body of the device as shown in FIG. 18 in order to provide the user with the program, but is also formed by the ROM 302 in which the program is recorded and which is provided to the user in a state in which it is incorporated in advance in the main body of the device, the hard disk included in the storage portion 308, or the like. The removable media 311 is formed by a magnetic disk (including a floppy disk) in which the program is recorded, an optical disk (including a compact disk-read only memory (CD-ROM) and a digital versatile disk (DVD)), a magneto optical disk (including a mini-disk (MD)), a semiconductor memory, or the like.

Note that, in this specification, steps that write the program to be recorded in the recording medium do not necessarily have to be performed in time series in line with the order of the steps, and instead may include processing that is performed in parallel or individually.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) An image processing device including:

a motion vector detection portion that performs comparison of a substantially spherical photographic subject such that, among a plurality of captured images including the photographic subject, an image as a processing target and another image as a comparison target are compared using each of the plurality of captured images as the processing target, and which detects a motion vector of a whole three-dimensional spherical model with respect to the processing target;

a motion compensation portion that performs motion compensation on the processing target, based on the motion vector of each of the plurality of captured images that is detected by the motion vector detection portion; and a synthesis portion that synthesizes each of the captured images that are obtained as a result of the motion compensation performed by the motion compensation portion.

(2) The image processing device according to (1), wherein with respect to each of a plurality of blocks that are divided up from the processing target, the motion vector detection portion detects a local motion vector by performing block matching with the comparison target, and wherein the motion vector detection portion detects the motion vector of the whole three-dimensional spherical model with respect to the processing target, using the local motion vector of each of the plurality of blocks.

(3) The image processing device according to (1) or (2), wherein the motion vector detection portion converts the local motion vector with respect to each of the plurality of blocks in the processing target into a local spherical motion vector in the three-dimensional spherical model, and wherein the motion vector detection portion detects the motion vector of the whole three-dimensional spherical model with respect to the processing target, using the local spherical motion vector of each of the plurality of blocks.

(4) The image processing device according to (1), (2), or (3)

wherein the motion vector detection portion converts each of the plurality of blocks in the processing target into a plurality of spherical blocks in the three-dimensional spherical model, wherein with respect to each of the plurality of spherical blocks, the motion vector detection portion detects, as the local motion vector, a local spherical motion vector by performing block matching with the comparison target, and wherein the motion vector detection portion detects the motion vector of the whole three-dimensional spherical model with respect to the processing target, using the local spherical motion vector of each of the plurality of spherical blocks.

(5) The image processing device according to any one of (1) to (4), wherein the motion vector detection portion converts each of the processing target and the comparison target into a spherical image in the three-dimensional spherical model, and wherein the motion vector detection portion performs matching between the spherical image of the processing target and the spherical image of the comparison target, and thereby detects the motion vector of the whole three-dimensional spherical model with respect to the processing target.

(6) The image processing device according to any one of (1) to (5), wherein the photographic subject is a fundus oculi.

(7) The image processing device according to any one of (1) to (6), wherein the three-dimensional spherical model is switched and used in accordance with conditions of the photographic subject.

(8) An image processing device including:

a conversion portion that, among a plurality of captured images that include a substantially spherical photographic subject, converts an image as a processing target and another image as a comparison target into spherical images on a three-dimensional spherical model, using each of the plurality of captured images as the processing target;

an extraction portion that extracts features of each of the spherical image of the processing target and the spherical image of the comparison target;

an alignment portion that aligns positions of the features such that the features match each other; and a synthesis portion that synthesizes each of the captured images that are obtained as a result of the alignment performed by the alignment portion.

(9) The image processing device according to (8), wherein a blood vessel shape is used as the feature.

(10) The image processing device according to (8) or (9), wherein the photographic subject is a fundus oculi.

(11) The image processing device according to (8), (9), or (10), wherein the three-dimensional spherical model is switched and used in accordance with conditions of the photographic subject.

The present technology can be applied to an image processing device.

The present disclosure contains subject matter related to that disclosed in Japanese Priority Patent Application JP 2011-188277 filed in the Japan Patent Office on Aug. 31, 2011, the entire content of which is hereby incorporated by reference.

What is claimed is:

1. An image processing device comprising:
one or more processors configured to:
compare a substantially spherical photographic subject such that, among a plurality of captured images including the photographic subject, an image as a processing target and another image as a comparison target are compared using each of the plurality of captured images as the processing target, and detect a motion vector of a whole three-dimensional spherical model with respect to the processing target;
perform motion compensation on the processing target, based on the detected motion vector of each of the plurality of captured images; and
synthesize each of the captured images that are obtained as a result of the motion compensation.

2. The image processing device according to claim 1, wherein the one or more processors are further configured to:
perform block matching with the comparison target:
detect a local motion vector with respect to each of a plurality of blocks that are divided up from the processing target based on the performed block matching with the comparison target; and
detect the motion vector of the whole three-dimensional spherical model with respect to the processing target, based on the detected local motion vector of each of the plurality of blocks.

3. The image processing device according to claim 2, wherein the one or more processors are further configured to:
convert the local motion vector with respect to each of the plurality of blocks in the processing target into a local spherical motion vector in the three-dimensional spherical model; and
detect the motion vector of the whole three-dimensional spherical model with respect to the processing target, based on the local spherical motion vector of each of the plurality of blocks.

4. The image processing device according to claim 2, wherein the one or more processors are further configured to:
convert each of the plurality of blocks in the processing target into a plurality of spherical blocks in the three-dimensional spherical model;
detect a local spherical motion vector, as the local motion vector, with respect to each of the plurality of spherical blocks, based on the performed block matching with the comparison target; and
the motion vector of the whole three-dimensional spherical model with respect to the processing target, based on the local spherical motion vector of each of the plurality of spherical blocks.

5. The image processing device according to claim 1, wherein the one or more processors are further configured to:
convert each of the processing target and the comparison target into a spherical image in the three-dimensional spherical model; and
perform matching between the spherical image of the processing target and the spherical image of the comparison target, and detect the motion vector of the whole three-dimensional spherical model with respect to the processing target.

6. The image processing device according to claim 1, wherein the photographic subject is a fundus oculi.

7. The image processing device according to claim 6, wherein the three-dimensional spherical model is switched and used in accordance with conditions of the photographic subject.

8. An image processing method comprising:
performing comparison of a substantially spherical photographic subject such that, among a plurality of captured images including the photographic subject, an image as a processing target and another image as a comparison target are compared using each of the plurality of captured images as the processing target, and detecting a motion vector of a whole three-dimensional spherical model with respect to the processing target;
performing motion compensation on the processing target, based on the motion vector of each of the plurality of captured images that is detected by processing of the motion vector detecting step; and
synthesizing each of the captured images that are obtained as a result of the motion compensation performed by processing of the motion compensating step.

9. A non-transitory computer-readable storage medium having stored thereon, a set of computer-executable instructions for causing a computer to perform steps comprising:
performing comparison of a substantially spherical photographic subject such that, among a plurality of captured images including the photographic subject, an image as a processing target and another image as a comparison target are compared using each of the plurality of captured images as the processing target, and detecting a motion vector of a whole three-dimensional spherical model with respect to the processing target;
performing motion compensation on the processing target based on the motion vector of each of the plurality of captured images; and
synthesizing each of the captured images that are obtained as a result of the motion compensation.

* * * * *